(12) United States Patent
Tonkovich et al.

(10) Patent No.: US 7,220,390 B2
(45) Date of Patent: May 22, 2007

(54) MICROCHANNEL WITH INTERNAL FIN SUPPORT FOR CATALYST OR SORPTION MEDIUM

(75) Inventors: Anna Lee Tonkovich, Marysville, OH (US); Dongming Qiu, Dublin, OH (US); Richard Q. Long, Columbus, OH (US); Barry L. Yang, Dublin, OH (US); Thomas Yuschak, Dublin, OH (US); Steven T. Perry, Galloway, OH (US)

(73) Assignee: Velocys, Inc., Plain City, OH (US)

( * ) Notice: Subject to any disclaimer, the term of this patent is extended or adjusted under 35 U.S.C. 154(b) by 496 days.

(21) Appl. No.: 10/440,053

(22) Filed: May 16, 2003

(65) Prior Publication Data

US 2004/0228781 A1    Nov. 18, 2004

(51) Int. Cl.
*B01D 50/00* (2006.01)
*B01J 10/00* (2006.01)
*F01N 3/00* (2006.01)

(52) U.S. Cl. ............... 422/172; 422/178; 422/188; 422/190; 422/198; 422/211

(58) Field of Classification Search .......... 422/172, 422/178, 188, 190, 198, 211
See application file for complete search history.

(56) References Cited

U.S. PATENT DOCUMENTS

| | | | |
|---|---|---|---|
| 4,392,362 A | 7/1983 | Little ................ | 62/514 |
| 4,516,632 A | 5/1985 | Swift et al. ........ | 165/167 |
| 5,309,637 A | 5/1994 | Moriarty ............ | 29/890.054 |
| 5,317,805 A | 6/1994 | Hoopman et al. .... | 29/890.03 |
| 5,611,214 A | 3/1997 | Wegeng et al. ...... | 62/498 |
| 5,727,618 A | 3/1998 | Mundinger et al. .. | 165/80.4 |
| 5,811,062 A * | 9/1998 | Wegeng et al. ...... | 422/129 |
| 5,858,314 A | 1/1999 | Hsu et al. .......... | 422/211 |
| 6,126,723 A | 10/2000 | Drost et al. ........ | 96/4 |
| 6,129,973 A * | 10/2000 | Martin et al. ....... | 428/166 |
| 6,192,596 B1 * | 2/2001 | Bennett et al. ...... | 34/76 |
| 6,200,536 B1 | 3/2001 | Tonkovich et al. ... | 422/177 |

(Continued)

FOREIGN PATENT DOCUMENTS

EP       1 311 341 B1    8/2001

(Continued)

OTHER PUBLICATIONS

Besser, Ronald S. "New Directions in Reactor Design Through Miniaturization". Sep. 13, 2002, Tulane Engineering Forum.

(Continued)

*Primary Examiner*—N. Bhat
(74) *Attorney, Agent, or Firm*—Renner, Otto, Boisselle & Sklar, LLP

(57) ABSTRACT

This invention relates to an apparatus, comprising: at least one process microchannel having a height, width and length, the height being up to about 10 mm, the process microchannel having a base wall extending in one direction along the width of the process microchannel and in another direction along the length of the process microchannel; at least one fin projecting into the process microchannel from the base wall and extending along at least part of the length of the process microchannel; and a catalyst or sorption medium supported by the fin.

39 Claims, 5 Drawing Sheets

U.S. PATENT DOCUMENTS

| | | | |
|---|---|---|---|
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,313,393 B1 | 11/2001 | Drost | 136/201 |
| 6,352,577 B1 | 3/2002 | Martin et al. | 96/4 |
| 6,381,846 B2 | 5/2002 | Insley et al. | 29/890.039 |
| 6,415,860 B1 | 7/2002 | Kelly et al. | 165/748 |
| 6,488,838 B1 | 12/2002 | Tonkovich et al. | 208/108 |
| 6,490,812 B1 * | 12/2002 | Bennett et al. | 34/433 |
| 6,508,862 B1 | 1/2003 | Tonkovich et al. | 95/106 |
| 6,540,975 B2 | 4/2003 | Tonkovich et al. | 423/659 |
| 6,675,875 B1 | 1/2004 | Vafai et al. | 165/80.4 |
| 6,746,651 B1 | 6/2004 | Ponzo et al. | 422/220 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,756,340 B2 | 6/2004 | Voskoboynikov et al. | 502/328 |
| 6,756,515 B2 | 6/2004 | Rende et al. | 585/444 |
| 6,764,660 B1 | 7/2004 | Wiede, Jr. et al. | 422/198 |
| 6,769,444 B2 | 8/2004 | Guzman et al. | 137/15.01 |
| 6,770,245 B2 | 8/2004 | Akporiaye et al. | 422/82.12 |
| 6,773,684 B2 | 8/2004 | Lesieur et al. | 422/198 |
| 2001/0018140 A1 | 8/2001 | Hermann et al. | 429/20 |
| 2002/0048541 A1 | 4/2002 | Schodel et al. | 422/198 |
| 2004/0076562 A1 * | 4/2004 | Manzanec et al. | 422/211 |
| 2004/0104010 A1 | 6/2004 | Kenny et al. | 165/80.4 |
| 2004/0107831 A1 | 6/2004 | Graham et al. | 95/96 |
| 2004/0123626 A1 | 7/2004 | Caze et al. | 65/17.2 |
| 2004/0125689 A1 | 7/2004 | Ehrfeld et al. | 366/165.1 |
| 2004/0127352 A1 | 7/2004 | Jin et al. | 502/322 |
| 2004/0130057 A1 | 7/2004 | Mehrabi et al. | 264/171.13 |
| 2004/0131345 A1 | 7/2004 | Kylberg et al. | 392/454 |
| 2004/0131507 A1 | 7/2004 | Saitmacher et al. | 422/111 |
| 2004/0131829 A1 | 7/2004 | Joseph et al. | 428/166 |
| 2004/0132832 A1 | 7/2004 | Espinoza et al. | 518/716 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |

FOREIGN PATENT DOCUMENTS

| | | | |
|---|---|---|---|
| EP | 0 904 608 B1 | | 12/2001 |
| WO | 97/32687 | | 12/1997 |
| WO | 98/55812 | | 12/1998 |
| WO | 00/06295 | | 2/2000 |
| WO | 01/10773 | A1 | 2/2001 |
| WO | 01/12312 | A2 | 2/2001 |
| WO | 01/54807 | A1 | 8/2001 |
| WO | 01/95237 | A2 | 12/2001 |
| WO | 02/14854 | A1 | 2/2002 |
| WO | 02/064248 | A2 | 8/2002 |
| WO | 02/064248 | A3 | 8/2002 |
| WO | 03/026788 | | 4/2003 |
| WO | 03/078052 | A1 | 9/2003 |
| WO | 03/106386 | A2 | 12/2003 |
| WO | 2004/016346 | A1 | 2/2004 |
| WO | 2004/045760 | | 6/2004 |
| WO | 2004/050799 | | 6/2004 |
| WO | 2004/052518 | | 6/2004 |
| WO | 2004/052530 | | 6/2004 |
| WO | 2004/052941 | | 6/2004 |
| WO | 2004/054013 | | 6/2004 |
| WO | 2004/054696 | | 7/2004 |
| WO | 2004/062790 | | 7/2004 |
| WO | 2004/062791 | | 7/2004 |
| WO | 2004/062792 | | 7/2004 |
| WO | 2004/067160 | | 8/2004 |
| WO | 2004/067444 | | 8/2004 |
| WO | 2004/067492 | | 8/2004 |
| WO | 2004/067708 | | 8/2004 |

OTHER PUBLICATIONS

Ouyang et al. "Flexible Microreactor System for Chemical Research at Moderate and High Temperatures". Stevens Institute of Technology.

International Preliminary Report on Patentability, Application No. PCT/US2004/010945, mailed Sep. 6, 2005.

Matlosz et al.; "Microreactors as Tools in Chemical Research"; Microreaction Technology; IMRET 5: Proceedings of the Fifth International Conference on Microreaction Technology. (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6-6th International Conference on Microreaction Technology; Mar. 14-20, 2002.

Wegeng et al.; "Compact Fuel Processors for Fuel Cell Powered Automobiles Based on Microchannel Technology"; Fuel Cells Bulletin No. 28; pp. 8-13.

Rostami et al.; "Flow and Heat Transfer for Gas Flowing in Microchannels: a Review"; Heat and Mass Transfer 38 (2002) 359-367.

Written Opinion and International Search Report, Application No. PCT/US2004/010945, mailed Sep. 27, 2004.

* cited by examiner

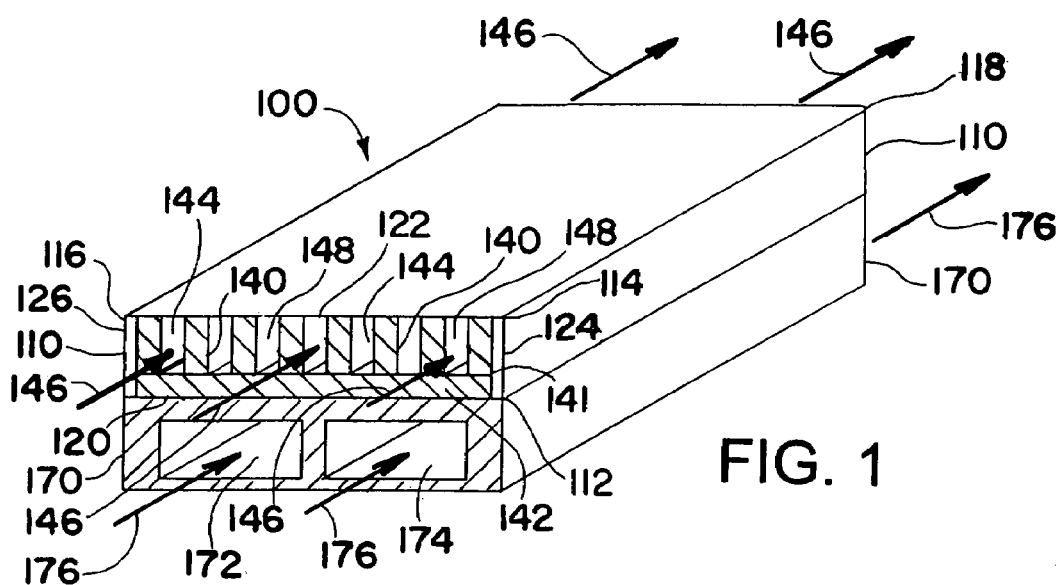
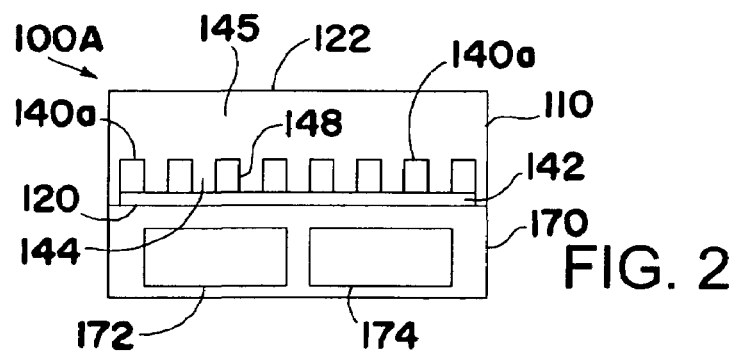
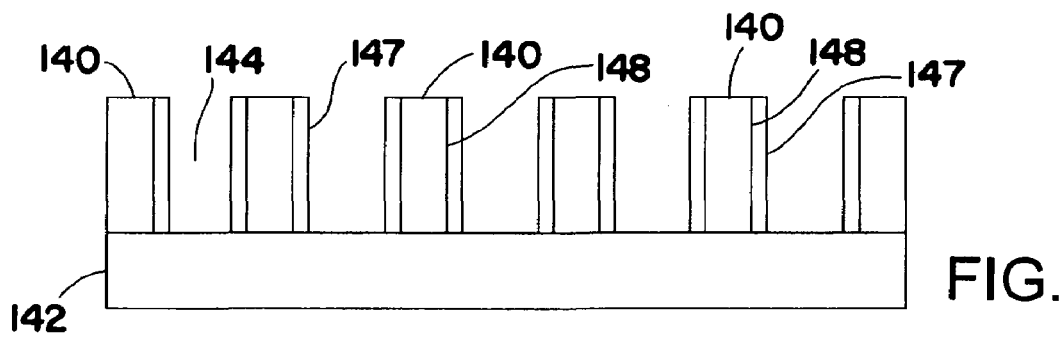
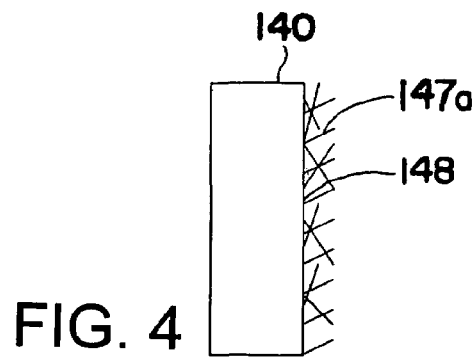 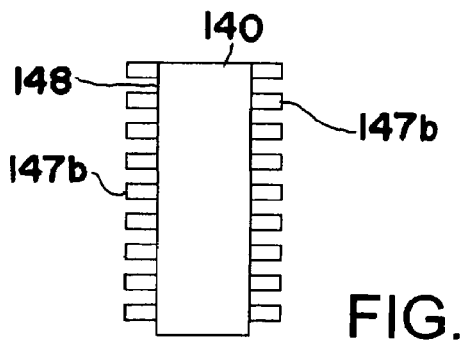

MICROCHANNEL WITH INTERNAL FIN SUPPORT FOR CATALYST OR SORPTION MEDIUM

TECHNICAL FIELD

This invention relates to microchannels containing an internal fin for supporting a catalyst or sorption medium. These microchannels are suitable for use in conducting catalytically activated chemical reactions and separating fluids using sorption mediums.

BACKGROUND OF THE INVENTION

Microchannel reactors may be used in a variety of catalytic processes wherein reactants contact a catalyst within the microchannel reactor and undergo reaction. The term "microchannel" is used herein to refer to a channel having an internal width or height up to about 10 mm. A problem with these microchannel reactors relates to the fact that for many processes it is difficult to provide adequate catalytic surface area for the process to operate effectively. Also, for many processes it is difficult to provide sufficiently short mass transport distances for the reactants to the catalytic surface area for the process to operate effectively.

One solution to these problems is to coat the interior walls of the microchannel with an intermediate layer of an inorganic oxide, called a washcoat, in order to provide a high surface area. The catalyst is then deposited on the surface of the washcoat. A problem with the use of these washcoats is that the additional surface area that is provided is not sufficient for many processes.

Another solution to this problem is to deposit the catalyst on a porous structure such as a foam, felt or wad which is then placed in the microchannel. The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. A problem with each of these support structures is that the thermal conductivity provided by these support structures is inadequate for many processes.

The present invention provides a solution to these problems. With the present invention, one or more internal fins for supporting a catalyst is provided wherein the fin provides enhanced surface area for the catalyst as well as enhanced thermal conductivity. The fins also provide short mass transport distances of the reactant to the catalytic surface where reaction occurs. In one embodiment of the invention, the internal fin provides the microchannel with enhanced structural stability.

A problem with microchannel reactors that are coupled with adjacent heat exchangers relates to the relatively high pressure drop that often occurs as a result of the small internal dimensions of the microchannels when high heat flux or high throughput is desired. If the microchannel height or width is maintained relatively small to overcome mass transport limitations, the pressure drop tends to increase in inverse proportion to the channel height or width, potentially limiting maximum throughput.

The present invention provides a solution to this problem by increasing the total cross-sectional area available for fluid flow through the microchannel from the minimum dimension needed to minimize or reduce the effect of mass transport limitations. If the fins project outwardly at right angles from the heat transfer surface from an adjacent heat exchanger, the height of the fins can be significantly greater than the gap size needed to minimize mass transport limitations as long as the spacing between adjacent fins is kept small enough to minimize the mass transport limitations. Taller fins enable lower pressure drop per unit length through the microchannel reactor. The thermal conductivity of the fin material and fin height can also be tailored to prevent heat transfer limitations for the reaction of interest. Since the distances over which the rate of thermal conduction become limiting are often much larger than the distances over which the rate of mass transport become limiting, fin height can often be extended well beyond the maximum gap allowed for the desired mass transport characteristics. Thus a lower pressure drop and/or a higher capacity per microchannel may be realized through the use of the present invention with no decrease in reaction performance.

The fins provided for herein are not only useful in providing support for catalysts for use within microchannel reactors, they are also useful in providing support for sorption medium for use in separation processes conducted in microchannels.

SUMMARY OF THE INVENTION

This invention relates to an apparatus, comprising: at least one process microchannel having a height, width and length, the height being up to about 10 mm, the process microchannel having a base wall extending in one direction along the width of the process microchannel and in another direction along the length of the process microchannel; at least one fin projecting into the process microchannel from the base wall and extending along at least part of the length of the process microchannel; and a catalyst or sorption medium supported by the fin.

BRIEF DESCRIPTION OF THE DRAWINGS

In the annexed drawings, like parts and features have like designations.

FIG. 1 is a schematic illustration of the inventive apparatus, the apparatus comprising a process microchannel, a fin assembly comprising a plurality of fins positioned within the microchannel, and a heat exchanger adjacent to the process microchannel.

FIG. 2 illustrates an alternate embodiment of the apparatus illustrated in FIG. 1.

FIG. 3 illustrates an alternate embodiment of the fin assembly illustrated in FIG. 1.

FIG. 4 illustrates an alternate embodiment of one of the fins illustrated in FIG. 1.

FIG. 5 illustrates another alternate embodiment of one of the fins illustrated in FIG. 1.

DETAILED DESCRIPTION OF THE INVENTION

Figure 6:
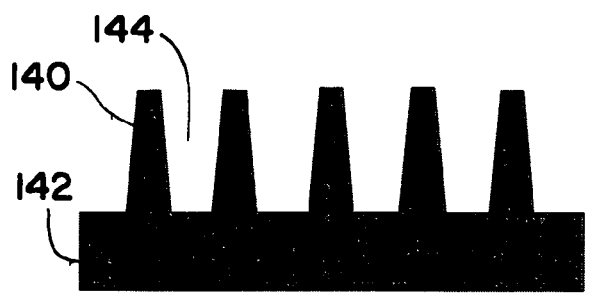
FIGS. 6–10 illustrate alternate embodiments of the fin assembly illustrated in FIG. 1.
Figure 7:
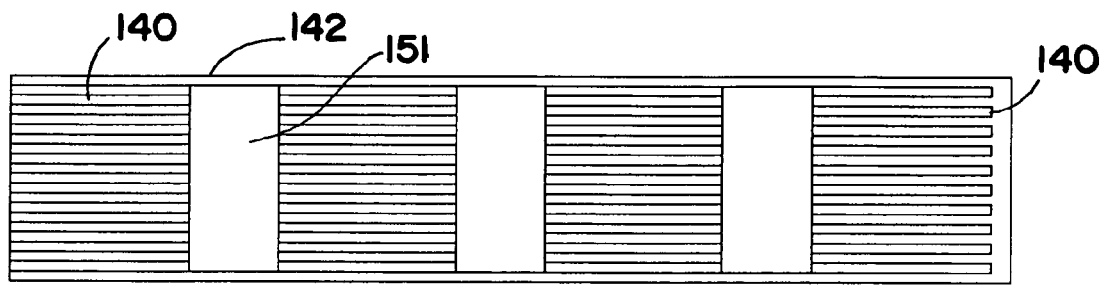
Figure 8:
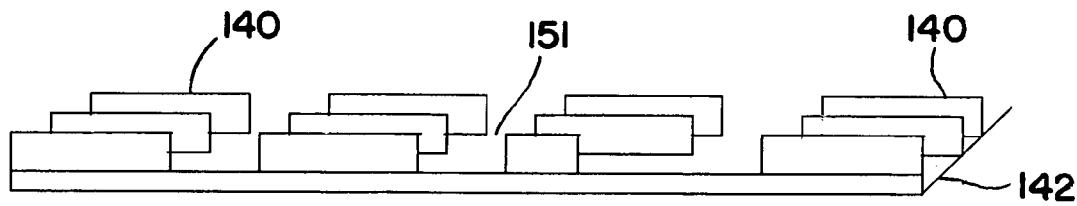

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. In one embodiment, the height or width is in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. Both height and width are perpendicular to the direction of flow through the microchannel.

The term "adjacent" when referring to the position of one channel relative to the position of another channel means directly adjacent such that a wall separates the two channels. This wall may vary in thickness. However, "adjacent" channels are not separated by an intervening fluid-containing channel that would interfere with heat transfer between the channels.

The term "fluid" refers to a gas, a liquid, or a gas or a liquid containing dispersed solids, or a mixture thereof. The fluid may be in the form of a gas containing dispersed liquid droplets.

The term "contact time" refers to the volume of the reaction zone within the microchannel reactor divided by the volumetric feed flow rate of the reactant composition at a temperature of 0° C. and a pressure of one atmosphere.

The term "residence time" refers to the internal volume of a space (e.g., the reaction zone within a microchannel reactor) occupied by a fluid flowing through the space divided by the average volumetric flowrate for the fluid flowing through the space at the temperature and pressure being used.

The term "reaction zone" refers to the space within the microchannel reactor wherein the reactants contact the catalyst.

The term "conversion of hydrocarbon reactant" refers to the hydrocarbon reactant mole change between the reactant composition and the product divided by the moles of the hydrocarbon reactant in the reactant composition.

The term "selectivity to desired product" refers to the moles of the desired oxygenate or nitrile produced divided by the moles of the desired oxygenate or nitrile produced plus moles of other products (e.g., CO, $CO_2$) produced multiplied by their respective stoichiometric factors. For example, for the oxidation of ethylene to ethylene oxide with carbon dioxide as an unwanted side product, the production of one mole of ethylene oxide and one mole of carbon dioxide would correspond to a selectivity of $100\times(1/(1+\frac{1}{2}))$ =67%.

The invention will describe initially with respect to FIG. 1. Referring to FIG. 1, the inventive apparatus 100 comprises a process microchannel 110, a fin assembly 141 comprising a plurality of parallel spaced fins 140 positioned within the process microchannel 110, and a heat exchanger 170 positioned adjacent to the process microchannel.

The process microchannel 110 has a height indicated in FIG. 1 by the vertical line extending from point 112 to point 114, a width indicated by the horizontal line extending from point 114 to 116, and a length indicated by the line extending from point 114 to 118. The process microchannel 110 has a base wall 120, and an upper wall 122 that is parallel to an opposite base wall 120. The process microchannel also has vertical walls 124 and 126 which connect walls 120 and 122.

The fins 140 are mounted on fin support 142 which overlies base wall 120. The fins 140 project from the fin support 142 into the interior of the process microchannel 110. The fins 140 extend to and contact the interior surface of upper wall 122. The fin channels 144 between the fins 140 provide passage ways for fluid to flow through the process microchannel 110 parallel to its length, as indicated by directional arrows 146. Each of the fins 140 has an exterior surface 148 on each of its sides, this exterior surface provides a support base for a catalyst or sorption medium. With a catalytic reaction, one or more fluid reactants flow through the fin channels 144 in the direction indicated by directional arrows 146, contact the catalyst supported on the exterior surface 148 of the fins 140, and react to form a product. With a fluid separation process, a fluid flows through the fin channels 144 in the direction indicated by directional arrows 146, contacts the sorption medium supported on the exterior surface 148 of the fins 140, and one or more components of the fluid are sorbed by the sorption medium.

Figure 12:
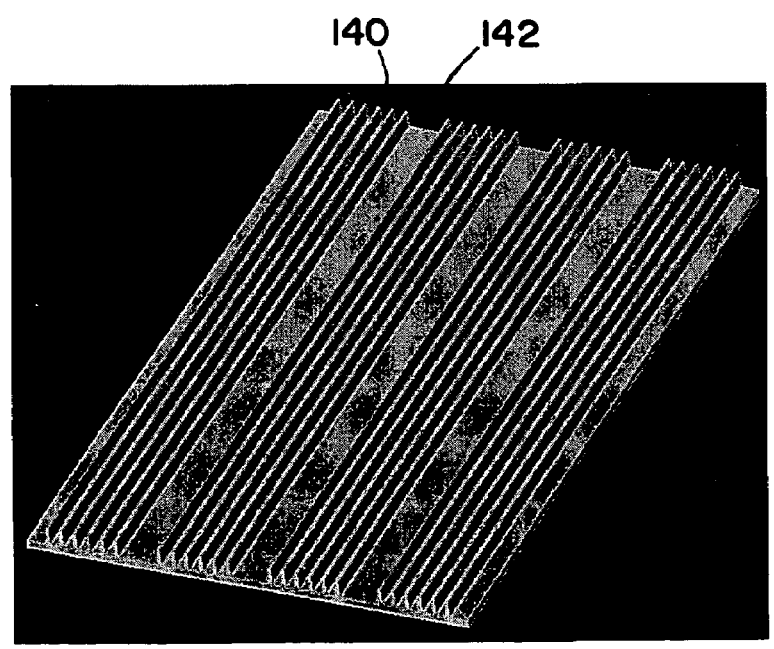
FIG. 12 illustrates an insertable fin assembly that can be used in making a plurality of adjacent process microchannel of the type illustrated in FIG. 1.

Each of the fins 140 may have a height ranging from about 0.02 mm up to the height of the process microchannel 110, and in one embodiment from about 0.02 to about 10 mm, and in one embodiment from about 0.02 to about 5 mm, and in one embodiment from about 0.02 to about 2 mm. The width of each fin may range from about 0.02 to about 5 mm, and in one embodiment from about 0.02 to about 2 mm and in one embodiment about 0.02 to about 1 mm. The length of each fin may be of any length up to the length of the process microchannel 110, and in one embodiment from about 5 mm to about 500 cm, and in one embodiment about 1 cm to about 250 cm, and in one embodiment about 1 cm to about 100 cm, and in one embodiment about 2 cm to about 25 cm. The gap between each of the fins 140 may be of any value and may range from about 0.02 to about 5 mm, and in one embodiment from about 0.02 to about 2 mm, and in one embodiment from about 0.02 to about 1 mm. The number of fins 140 in the process microchannel 110 may range from about 1 to about 50 fins per centimeter of width of the process microchannel 110, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. Each of the fins may have a cross-section in the form of a rectangle or square as illustrated in FIGS. 1–5, or a trapezoid as illustrated in FIGS. 6 and 12. When viewed along its length, each fin 140 may be straight, tapered or have a serpentine configuration. The fins 140 may be made of any material that provides sufficient strength, dimensional stability and heat transfer characteristics to permit operation for which the process microchannel 110 is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin 140 may be made of an alumina forming material such as FeCrAlY, such that when oxidized the skin forms alumina. The alumina skin is particularly suitable for accepting support coatings for catalysts or sorbent materials.

Heat exchanger 170 is positioned adjacent to process microchannel 110 and includes heat exchange channels 172 and 174. The heat exchange channels 172 and 174 are adapted for heat exchange fluid to flow through the channels in a longitudinal direction parallel to the flow of fluid through the process microchannel 110 as indicated by directional arrows 176. When the heat exchange fluid flows in the direction indicated in FIG. 1, it flows in a direction that is cocurrent with the flow of fluid through the process microchannel 110. Alternatively, the heat exchange fluid could flow through the heat exchange channels 172 and 174 in a direction opposite to the direction shown in FIG. 1, and thus flow countercurrent to the flow of fluid through the process microchannel 110. Alternatively, the heat exchange channels 172 and 174 could be oriented at a ninety degree angle relative to the process microchannel 110 to provide for the flow of heat exchange fluid in a direction that is crosscurrent relative to the flow of the fluid through the process microchannel 110.

Although only a single process channel 110 and two heat exchange channels 172 and 174 are illustrated in FIG. 1 for use in the apparatus 100, there is practically no upper limit to the number of process microchannels 110, and heat exchange channels 172 and 174 that can be used in the apparatus 100. For example, the apparatus 100 may contain two, four, six, eight, ten, twenty, fifty, one hundred, hundreds, one thousand, thousands, ten thousand, tens of thousands, one hundred thousand, hundreds of thousands, millions, etc., of the process microchannels and heat exchange channels.

The process microchannels 110 may be arranged in parallel, for example, in arrays of planar microchannels. The microchannels may be of the microcomponent sheet architecture variety such as disclosed in U.S. Pat. No. 6,200,536B1, which is incorporated herein by reference. Each of the process microchannels 110 may have a height of up to about 10 mm, and in one embodiment from about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The width may be of any value, for example, it may range from about 0.1 cm to about 100 cm, and in one embodiment from about 0.1 cm to about 75 cm, and in one embodiment from about 0.1 cm to about 50 cm, and in one embodiment about 0.2 cm to about 25 cm. The length of each of the process microchannels 110 may be of any value, for example, the length may range from about 1 cm to about 500 cm, and in one embodiment 1 cm to about 250 cm, and in one embodiment 1 cm to about 100 cm, and in one embodiment 1 cm to about 50 cm, and in one embodiment about 2 to about 25 cm.

The process microchannels 110 may be made of any material that provides sufficient strength, dimensional stability and heat transfer characteristics to permit operation of the processes for which they are intended. These materials include steel (e.g., stainless steel, carbon steel, and the like); monel; inconel; aluminum, titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

Each of the heat exchange channels 172 and 174 may have at least one internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment about 0.5 to about 1 mm. The other internal dimension may range from about 1 mm to about 1 m, and in one embodiment about 1 mm to about 0.5 m, and in one embodiment about 2 mm to about 10 cm. The length of the heat exchange channels may range from about 1 mm to about 1 m, and in one embodiment about 1 cm to about 0.5 m. The separation between each process microchannel 110 and the next adjacent heat exchange channel 172 or 174 may range from about 0.05 mm to about 5 mm, and in one embodiment about 0.2 mm to about 2 mm.

The heat exchanger 170 may be made of any material that provides sufficient strength, dimensional stability and heat transfer characteristics to permit operation for which it is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The apparatus 100 has appropriate headers, footers, valves, conduit lines, control mechanisms, etc., to control the input and output of process fluids and heat exchange fluids. These are not shown in FIG. 1, but can be provided by those skilled in the art.

The apparatus 100A illustrated in FIG. 2 is identical to the apparatus 100 illustrated in FIG. 1 with the exception that the fins 140 are replaced by partial fins 140a. The partial fins 140a in FIG. 2 extend only part way from the fin support 142 to the upper wall 122. The height of the partial fins 140a may range from about 1% to about 99% of the gap between the fin support 142 and the upper wall 122, and in one embodiment from about 5% to about 95%, and in one embodiment from about 10% to about 90%, and in one embodiment from about 20% to about 80%. An advantage of using the partial fins 140a is the additional space 145 that is provided in the process microchannel 110 facilitates the use of staged oxygen or air addition which is useful for certain processes such as combustion or selective oxidation reactions. The partial fins 140a permit the oxygen or air to enter the fin channels 144. An additional advantage of the partial fins 140a is reduced pressure drop for the fluids flowing through the process microchannel 110 as a result of providing the additional space 145 for flow.

The fins 140 may have a porous material overlying part or all of the exterior surface 148. This is illustrated in FIG. 3 wherein porous material 147 overlies exterior surface 148 of fin 140. The porous material may be in the form of a coating, fibers, felt, foam, or other non-dense substrate. The pore size openings may range from about 3 angstroms to about 100 microns. The catalyst or sorption medium may be deposited on the porous material.

The exterior surface 148 of the fins 140 may include surface enhancers such as random fibers 147a extending from exterior surface 148 as illustrated in FIG. 4, or protrusions 147b extending from exterior surface 148 as illustrated in FIG. 5. The fibers 147a and protrusions 147b may have lengths ranging from about 0.001 to about 0.3 mm, and in one embodiment from about 0.01 to about 0.1 mm. The catalyst or sorption medium may be deposited on the fibers 147a or protrusions 147b.

The fins 140 may either be continuous or discontinuous along the direction of flow as indicated in FIGS. 7–10. Advantages of discontinuous fins include the ability of providing a thermal block to reduce the contribution of axial conduction. Another advantage is the ability to integrate a fin structure into process microchannel employing staged oxidant addition along the length of the channel. The section 151 (FIGS. 7 and 8) with no fins may be positioned next to an oxidant inlet port, jet, nozzle, or other mechanism for introducing the oxidant into the process microchannel. The oxidant can then fully or partially mix with the fluids flowing through the process microchannel before entering the next fin region.

Figure 9:
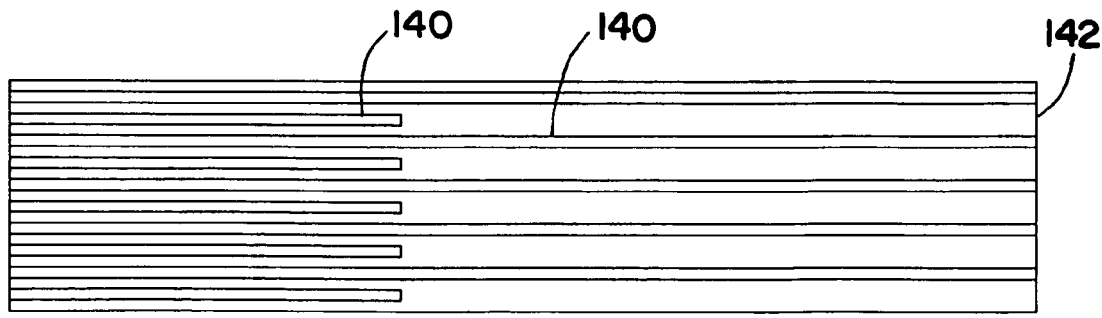

In one embodiment, the fins 140 may not all be the same length as illustrated in FIG. 9. Some fins 140 may extend down the entire length of the process microchannel 110 while other fins may extend only part way. This embodiment is advantageous for some reactions where the mass transfer resistance is highest at the front of the reaction zone. The more closely spaced fins reduce the transport distance of reactants to the catalyst or sorbent wall. The mass transfer time is roughly equal to the diffusion distance squared divided by the mass diffusivity. As the reaction or sorption proceeds, there may not be a need to continue this close spaced fin arrangement down the length of the zone. This has the advantage of reducing the overall pressure drop. An additional advantage is the enhanced heat transfer that is present where the fins are more closely spaced. It may be advantageous to transfer considerable more heat near the front of the reaction zone where the concentration of the reactants are highest. The additional fins add extra heat transfer surface area plus the reduced hydraulic diameter further increases the local convective heat transfer coefficient.

Figure 10:
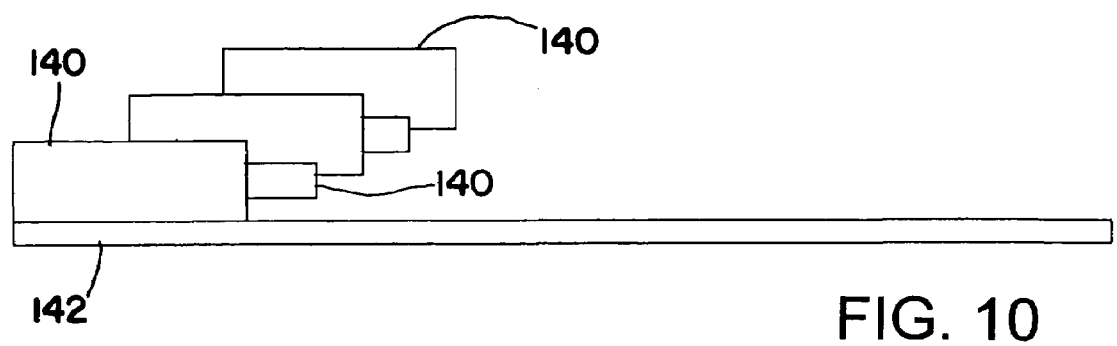

An alternate embodiment is the use of fins 140 with different heights as illustrated in FIG. 10. Some fins may be relatively tall, while others are relatively short. The relatively tall fins may contact the upper wall 122, while others fill only part (for example, about 10% to about 90%) of the gap or height of the process microchannel 110. An advantage of this configuration is that it provides a reduction in overall pressure drop by reducing occlusions to flow. This configuration may be used with some processes that require only a modest enhancement to surface area for either heat or mass transport.

Figure 11:
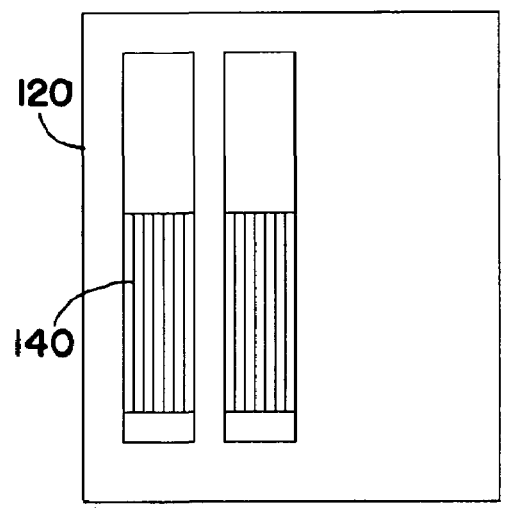
FIG. 11 illustrates a plurality of fins formed in the base wall of the process microchannel illustrated in FIG. 1.

The fins 140 may be directly formed in the base wall 120 as opposed to being inserted within the process microchannel 100. These fins may be formed using a slitting saw, photochemical machining, or electrochemical machining. As shown in FIG. 11, the flow path for the process may include a channel that is not occluded in one section and then enters a reaction or sorption zone containing fins. The fins may extend from one end of the base wall 120 to the other end, or they may alternately be stopped short within the base wall 120.

Fins that are formed ex situ and then placed within the process microchannel 110, may be made wide enough to fill one microchannel at a time, or they may be made wider to simultaneously fill multiple microchannels. FIG. 12 illustrates an example of a fin assembly that spans four process microchannels. These fins may be inserted during stacking of laminate sheets and then diffusion bonded to form an integral component. An advantage of these fins is that they provide additional support for the microchannel walls during bonding. The fins may alternatively be inserted after diffusion bonding and removed for refurbishment or replacement after operation of the process microchannels.

The catalyst or sorption medium may be deposited on the exterior surface 148, porous material overlying the exterior surface, or on the surface enhancers illustrated in FIGS. 4 and 5 using conventional techniques. These include washcoating the catalyst or sorption medium on the fin surface, growing the catalyst or sorption medium on the fin surface from solution, or depositing the catalyst or sorption medium on the fin surface using vapor deposition. The vapor deposition may be chemical vapor deposition or physical vapor deposition.

The catalyst may comprise any catalyst that is suitable for use in chemical reactors involving the use of fluid reactants. The catalyst may be a catalyst useful in conducting one or more of the following chemical reactions: acetylation addition, alkylation, dealkylation, hydrodealkylation, reductive alkylation, amination, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, ammoxidation, water-gas shift, dehalogenation, dimerization, epoxidation, esterification, Fischer-Tropsch reaction, halogenation, hydrohalogenation, homologation, hydration, dehydration, hydrogenation, dehydrogenation, hydrocarboxylation, hydroformylation, hydrogenolysis, hydrometallation, hydrosilation, hydrolysis, hydrotreating, isomerization, methylation, demethylation, metathesis, methanol synthesis, nitration, oxidation, partial oxidation, polymerization, reduction, reformation, reverse water gas shift, sulfonation, telomerization, transesterification, trimerization, Sabatier reaction, carbon dioxide reforming, preferential oxidation, or preferential methanation.

The catalyst may comprise a metal, metal oxide or mixed metal oxide of a metal selected from Mo, W, V, Nb, Sb, Sn, Pt, Pd, Cs, Zr, Cr, Mg, Mn, Ni, Co, Ce, or a mixture of two or more thereof. These catalysts may also comprise one or more alkali metals or alkaline earth metals or other transition metals, rare earth metals, or lanthanides. Additionally elements such as P and Bi may be present.

The catalyst may comprise one or more: catalyst metals, including noble metals, transition metals and combinations thereof; metal oxides, including oxides of alkali metals, alkaline earth metals, boron, gallium, germanium, arsenic, selenium, tellurium, thallium, lead, bismuth, polonium, magnesium, titanium, vanadium, chromium, manganese, iron, nickel, cobalt, copper, zinc, zirconium, molybdenum, tin, calcium, aluminum, silicon, lanthanum series element(s), and combinations thereof; composites; zeolite(s); nitrides; carbides; sulfides; halides; phosphates; and combinations of any of the above.

The catalyst may comprise an oxidation catalyst represented by the formula

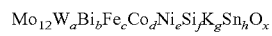

$$Mo_{12}W_aBi_bFe_cCo_dNi_eSi_fK_gSn_hO_x$$

in which: a is between 0 and 5, b is between 0.5 and 5, c is between 0.1 and 10, d is between 0.5 and 10, e is between 0 and 10, f is between 0 and 15, g is between 0 and 1, h is between 0 and 2, and x is the quantity of oxygen bonded to the other elements and depends on their oxidation states. These catalysts are described in U.S. Pat. No. 6,251,821 B1 as being useful for making acrolein from propylene by oxidation. This patent is incorporated herein by reference.

The catalyst may comprise an oxidation catalyst represented by the formula

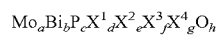

$$Mo_aBi_bP_cX^1_dX^2_eX^3_fX^4_gO_h$$

wherein $X^1$ is V, Nb, Ta, Cr, W, Ga, Ce and/or La; $X^2$ is Li, Na, K, Rb, Cs, Cu, Ag, Au, Pd and/or Pt; $X^3$ is Sn, Pb, Sb, Bi, Te, Fe, Co and/or Ni; $X^4$ is Si, Al, Ti and/or Zr; a is 0 to 2; d is 0 to 2, with the proviso that the sum of a and d is at least 0.20; b is 0 to 1.5, c is 0 to 10, with the proviso that the sum of b and c is at least 0.1; e is 0 to 0.5, f is 0 to 0.5, g is 0 to 20 and h is a number different from zero which is determined by the valence and frequency of the elements different from oxygen. This catalyst is disclosed in U.S. Pat. No. 6,252,122 B1 as being useful for converting propane to acrolein. This patent is incorporated herein by reference.

The catalyst may comprise an oxidation catalyst represented by the formula $$Mo_{12}Bi_aFe_bX_c^1X_d^2X_e^3X_f^4O_n$$

where $X^1$ is Ni and/or Co; $X^2$ is Tl, an alkali metal and/or an alkaline earth metal; $X^3$ is Zn, P, As, B, Sb, Sn, Ce, Pb, and/or W; $X^4$ is Si, Al, Ti and/or Zr; a is from 0.5 to 5; b is from 0.01 to 5, and in one embodiment from 2 to 4; c is from 0 to 10, and in one embodiment from 3 to 10; d is from 0 to 2, and in one embodiment from 0.02 to 2; e is from 0 to 8, and in one embodiment from 0 to 5; f is from 0 to 10; and n is a number which is determined by the valency and frequency of the elements other than oxygen. These catalysts are disclosed in U.S. Pat. No. 6,395,936 B1 as being useful for the oxidation of propylene to acrolein. This patent is incorporated herein by reference.

The catalyst may comprise an oxidation catalyst represented by the formula $$[Bi_nA_aO_x][(100-z)\% \ E_eFe_fNi_gMo_mO_y+z \% \ SiO_2]$$

wherein A is at least one element selected from the group consisting of B, P and Mo; E is at least one element having the atomic valence of 2; when m is 1, n is 0.001 to 3, a is 0 to 3, e is 0 to 3, f is 0.01 to 5, g is 0.1 to 5, and z is 0 to 90; and x and y are numbers such that the valence requirements of the other elements for oxygen in the core and shell catalytic phase, respectively, are satisfied. This catalyst is disclosed in U.S. Pat. No. 6,410,800 B1 as being useful for the oxidation of propylene to acrolein. This patent is incorporated herein by reference.

The catalyst may comprise an oxidation catalyst represented by the formulae $$Mo_{12}Co_{3.5}B_{1.1}Fe_{0.8}W_{0.5}Si_{1.4}K_{0.05}O_x$$

or $$Ni_{2.1}Co_{3.5}Fe_{2.6}P_{0.43}Bi_{1.0}Mo_{9.3}Mn_{0.15}Cr_{0.09}Ba_{0.07}Zr_{0.0012}K_{0.07}O_x$$

where x is the quantity of oxygen bonded to the other elements and depends on their oxidation state. These catalysts are disclosed in U.S. Pat. No. 6,437,193 B1 as being useful for the oxidation of propylene to acrolein. This patent is incorporated herein by reference.

The catalyst may comprise an oxidation catalyst represented by the formula $$Bi_bMo_cV_vA_aD_dE_eO_x$$

wherein A is one or more of K, Na, Li, Cs and Tl; D is one or more of Fe, Ni, Co, Zn, Ce or La; E is one or more of W, Nb, Sb, Sn, P, Cu, Pb, B, Mg, Ca or Sr; a, d and e are each 0 to 10; b is 0.1 to 10; c is 0.1 to 20; v is 0.1 to 10; c:b is from 2:1 to 30:1; v:b is from 1.5 to 8:1; and x is determined by the frequency and the valence of the elements other than oxygen in the above formula. This catalyst is disclosed in U.S. Pat. No. 5,198,580 as being useful for the conversion of propane to acrylic acid, propylene, acrolein and acetic acid.

The catalyst may comprise an oxidation catalyst represented by the formula $$M_a^1Mo_{1-b}M_b^2O_x$$

where $M^1$ is Co, Ni, Mg, Zn, Mn and/or Cu; $M^2$ is W, V, Te, Nb, P, Cr, Fe, Sb, Ce, Sn and/or La; a is from 0.5 to 1.5, b is from 0 to 0.5; and x is a number which is determined by the valency and frequency of the elements other than oxygen. These catalysts are disclosed in U.S. Pat. Nos. 6,388,129 B1; 6,423,875 B1; and 6,426,433 B1 as being useful for the conversion of propane to acrolein and/or acrylic acid. These patents are incorporated herein by reference.

The catalyst may comprise an oxidation catalyst represented by the formula $$A_aB_bC_cCa_dFe_eBi_fMo_{12}O_x$$

where A is one or more of Li, Na, K, Rb or Cs; B is one or more of Mg, Sr, Mn, Ni, Co or Zn; C is one or more of Ce, Cr, Al, Sb, P, Ge, Sn, Cu, V or W; a is 0.01 to 1.0; b and e are 1.0 to 10; c is 0 to 5.0, and in one embodiment 0.05 to 5.0, and in one embodiment 0.05 to 4.0; d and f are 0.05 to 5.0; and x is a number determined by the valence requirements of the other elements present. These catalysts are disclosed in U.S. Pat. No. 6,268,529 B1 as being useful for the conversion of propane to acrolein and acrylic acid. This patent is incorporated herein by reference.

The catalyst may comprise an oxidation catalyst represented by the formula $$Mo_{12}V_{4.8}Sr_{0.5}W_{2.4}Cu_{2.2}O_x$$

where x is the quantity of oxygen bonded to the other elements and depends on their oxidation state. This catalyst is disclosed in U.S. Pat. No. 6,310,240 B1 as being useful in the conversion of acrolein to acrylic acid. This patent is incorporated herein by reference.

The catalyst may comprise an oxidation catalyst represented by the formula $$Mo_aW_bV_cA_dB_eO_x$$

wherein A is Fe, Cu, Bi, Cr, Sn, Sb, Ni, Co, Mn, Ce or Tl; B is an alkali or alkaline earth metal; and a, b, c, d, e and x respectively indicate the atomic ratio for Mo, W, V, A, B and O. When a is 10, b is 1.5 to 4, c is 1 to 5, d is 1 to 4, e is 0 to 2, and x is determined according to oxidation states of the other elements. This catalyst is disclosed in U.S. Pat. No. 6,384,275 B2 as being useful for the conversion of acrolein to acrylic acid. This patent is incorporated herein by reference.

The catalyst may comprise an oxidation catalyst represented by the formula $$Mo_{12}V_aX_b^1X_c^2X_d^3X_e^4X_f^5X_g^6O_n$$

where $X^1$ is W, Nb, Ta, Cr and/or Ce; $X^2$ is Cu, Ni, Co, Fe, Mn and/or Zn; $X^3$ is Sb and/or Bi; $X^4$ is one or more alkali metals; $X^5$ is one or more alkaline earth metals; $X^6$ is Si, Al, Ti and/or Zr; a is from 1 to 6; b is from 0.2 to 4; c is from 0.5 to 18; d is from 0 to 40; e is from 0 to 2; f is from 0 to 4; g is from 0 to 40 and n is a number which is determined by the valency and frequency of the elements other than oxygen. This catalyst is disclosed in U.S. Pat. No. 6,403,829 B2 as being useful for the conversion of acrolein to acrylic acid. This patent is incorporated herein by reference.

The catalyst may comprise an oxidation catalyst represented by the formula $$Mo_aV_bW_cCu_dX_eO_g$$

wherein X is at least one element selected from the group consisting of Mg, Ca, Sr and Ba, and a, b, c, d, e, and g are atomic ratios respectively of Mo, V, W, Cu, X and O such that when a is 12, b is in the range of 2 to 14, c in the range of 0 to 12, d in the range of 0 to 6 excluding 0 (0.1 to 6, for example), e is in the range of 0 to 3, and g is a numeral to be determined by the oxidized states of the elements. This catalyst is disclosed in U.S. Pat. No. 6,429,332 B1 as being useful for the conversion of acrolein to acrylic acid. This patent is incorporated herein by reference.

The catalyst may comprise an oxidation catalyst represented by the formula $$Mo_aW_bBi_cFe_dA_eB_fC_gD_hE_iO_x$$

wherein: A is Ni or Co; B is Na, K, Rb, Cs or Tl; C is an alkaline earth metal; D is P, Te, Sb, Sn, Ce, Pb, Nb, Mn, As, B or Zn; and E is Si, Al, Ti or Zr. When a is 12, b is from 0 to 10, c is from 0 to 10, d is from 0 to 10, e is from 2 to 15, f is from 0 to 10, g is from 0 to 10, h is from 0 to 4, I is from 0 to 30, and x is determined by the degree of oxidation of each of the elements. This catalyst is disclosed in U.S. Pat. No. 6,383,973 B1 as being useful for the conversion of propylene, isobutylene, t-butanol or methyl-t-butyl ether to (meth)acrolein or (meth)acrylic acid. This patent is incorporated herein by reference.

The catalyst may comprise an oxidation catalyst represented by the formula $$Mo_aP_bA_cB_dC_eD_fO_x$$

wherein A is at least one element selected from the group consisting of As, Sb, Ge, Bi, Zr, Ce and Se; B is at least one element selected from the group consisting of Cu, Fe, Cr, Ni, Mn, Co, Sn, Ag, Zn, Pd, Rh and Te; C is at least one element selected from the group consisting of V, W and Nb; D is at least one element selected from the group consisting of alkali metals, alkaline earth metals and Tl, and a, b, c, d, e, f, and x are atomic ratios respectively of Mo, P, A, B, C, D, and O such that when a is 12, b is a numeral in the range of 0.5 to 4, and in one embodiment 0.5 to 3; c is in the range of 0 to 5, and in one embodiment 0.01 to 3; d in the range of 0 to 3, and in one embodiment 0.01 to 2; e is in the range or 0 to 4, and in one embodiment 0.01 to 3; f is in the range or 0.01 to 4, and in one embodiment 0.01 to 3, and x is a numeral to be determined by the oxidized states of the elements. This catalyst is disclosed in U.S. Pat. No. 5,618,974 as being useful for the conversion of methacrolein, isobutyl aldehyde, or isobutyric acid to methacrylic acid. This patent is incorporated herein by reference.

The catalyst may comprise an oxidation catalyst containing Mo, V, Nb and Pd, or Mo, La, V and Pd. Specific examples include $$MoV_{0.396}Nb_{0.128}Pd_{0.000384}$$

and $$MoV_{0.628}Pd_{0.000288}La_{0.00001}$$

These catalysts are disclosed in U.S. Pat. No. 6,274,764 B1, which is incorporated herein by reference.

U.S. Pat. No. 6,143,921, which is incorporated herein by reference, discloses three oxidation catalysts, any one of which may be used with the inventive process. The first catalyst is represented by the formula $Mo_aV_bNb_cPd_d$, wherein: a is 1 to 5; b is 0 to 0.5; c is 0.01 to 0.5; and d is 0 to 0.2. The numerical values of a, b, c and d represent the relative gram-atom ratios of the elements Mo, V, Nb and Pd, respectively, in the catalyst. The elements are present in combination with the oxygen in the form of various oxides.

The second catalyst has a composition comprising the elements Mo, V, Pd, Nb, La, and X where X is Al, Ga, Si or Ge in the form of oxides in the ratio $Mo_aV_bLa_cPd_dNb_eX_f$, wherein: a is 1; b is 0.01 to 0.9; c is >0 to 0.2; d is >0 to 0.2; e is >0 to 0.2; and f is >0 to 0.3. The third catalyst is formed from a calcined composition represented by the formula $Mo_aV_bNb_cX_d$, wherein X is at least one promoter element selected from the group consisting of: P, B, Hf, Te and As; a is about 1 to 5; b is 1; c is about 0.01 to 0.5; and d is about 0 to 0.1.

The catalyst may be an oxidation catalyst which comprises in combination with oxygen the elements molybdenum, vanadium, niobium and gold according to the formula:

$$Mo_aW_bAu_cV_dNb_eY_f$$

wherein: Y is one or more elements selected frm the group consisting of Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te, La and Pd; a, b, c, d, e and f represent the gram atom ratios of the elements such that $0<a\leq1$; $0\leq b<1$; $a+b=1$; $10^{-5}<c\leq0.02$; $0<d\leq2$; $0<e\leq1$; and $0<f\leq2$. This catalyst is disclosed in U.S. Pat. No. 6,333,444 B1 as being useful for the oxidation of ethane or ethylene to acetic acid. This patent in incorporated herein by reference.

The catalyst may be an oxidation catalyst having a calcined composition represented by the formula $Mo_aV_bNb_cPd_d$, wherein: 1 is 1 to 5; b is 0 to 0.5; c is 0.01 to 0.5; and d is 0 to 0.2. This catalyst is disclosed in U.S. Pat. No. 6,383,977 B1 for converting ethane to acetic acid. This patent is incorporated herein by reference.

U.S. Pat. No. 6,441,227 B1, which is incorporated herein by reference, discloses two oxidation catalysts which can be used separately or in combination with each other in the inventive process. The first catalyst is a mixed metal oxide represented by formula $$Mo_aPd_bBi_cFe_dX^1_eX^2_fX^3_gO_z$$

wherein: $X^1$ is at least one or more of Co, Ni, V, Pt or Rh; $X^2$ is at least one or more of Al, Ga, Ge, Mn, Nb, Zn, Ag, P, Si or W; $X^3$ is at least one or more of K, Mg, Rb, Ca, Sr, Ba, Na or In; O is oxygen, and a is 1; $0<b\leq0.3$; $0<c\leq0.9$; $0<d\leq0.9$; $0<e\leq0.9$; $0<f\leq0.9$; $0<g\leq0.3$; and z is a number which satisfies the valences of the other elements in the formula. This catalyst is described as being useful for converting olefins to alpha-beta unsaturated aldehydes. The second catalyst is a metal oxide represented by the formula $$Mo_{a1}V_{b1}Al_{c1}X_{d1}Y_{e1}O_{z1}$$

wherein X is W or Mn or both; Y is at least one or more of Pd, Sb, Ca, P, Ga, Ge, Si, Mg, Nb or K; O is oxygen, and a, is 1; b, is 0.01 to 0.9; $0<c_1\leq0.2$; $0<d_1\leq0.5$; $0<e_1\leq0.5$; and $z_1$ is a number which satisfies the valences of the other elements in the formula. This catalyst is described as being suitable for converting an alpha-beta unsaturated aldehyde to an alpha-beta unsaturated carboxylic acid.

The catalyst may comprise an ammoxidation catalyst represented by the formula $$A_aK_bCs_cMg_dNi_eFe_fBi_gMo_{12}O_x$$

wherein A is one or more of the elements selected from Co, Mn, Cr, P, Sb, Te, Na, Ce or W, a is a number from 0 to 5; b is a number from 0 to 0.4; c is a number from 0 to 0.4, provided that the sum of b and c is from 0.1 to 0.4; d, e, f, and g are numbers from about 0.2 to 10, and x is a number determined by the valence requirements of the other elements. This catalyst is disclosed in U.S. Pat. No. 5,093,299 as being useful for the conversion of an olefin (e.g., propylene or isobutylene) to the corresponding unsaturated nitrile (e.g., acrylonitrile or methacrylonitrile) by reacting the olefin, ammonia and oxygen in the presence of the foregoing catalyst. This patent is incorporated herein by reference.

The catalyst may comprise an ammoxidation catalyst represented by the formula $$VSb_aM_mN_nO_x$$

where a is 0.5 to 2; M is one or more of Sn, Ti, Fe or Ga; m is 0.05 to 3; N is one or more of: W, Bi, Mo, Li, Mg, P, Zn, Mn, Te, Ge, Nb, Zr, Cr, Al, Cu, Ce or B; n is 0.0 to 0.5; and x is a number determined by the degree of oxidation of each of the other elements. This catalyst is disclosed in U.S. Pat. No. 5,258,543 as being useful for the ammoxidation of $C_3$ to $C_5$ monoolefins to alpha, beta-monounsaturated acyclic nitrites (e.g., acrylonitrile) having 3 to 5 carbon atoms.

U.S. Pat. No. 6,486,091 B1, which is incorporated herein by reference, discloses an ammoxidation catalyst represented by the formula $$Bi_aMo_bV_cSb_dNb_eA_fB_gO_x$$

wherein: A is one or more elements selected from groups VB (e.g., V, Nb, Ta), VIB (e.g., Cr, Mo, W), VIIB (e.g., Mn, Tc, Re) or VIII (e.g., Fe, Co, Ni) of the periodic table; B is at least one alkali promoter selected from groups IA (e.g., Li, Na, K) or IIA (e.g., Mg, Ca) of the periodic table; a is 0.01 to 12; b is 0.01 to 12; c is 0.01 to 2; d is 0.01 to 10; e is 0.01 to 1; f is 0 to 2; g is 0 to 1; and x is the number of oxygen atoms required to satisfy the valency requirements of the elements present. This catalyst is described as being useful for converting olefins to unsaturated nitriles.

The sorption medium may comprise metal ions that are complexed (e.g., chelated) by ligands. The metal ions may complex with $O_2$, or other fluid components to be separated. The metal ions that may be used include Fe(II), Co(II), Cu(I), V(II), Mn(II), Mn(III), Cr(II), Ag(I), Rh(I), Rh(II), Rh(III), U(IV), V(IV), Ru(II), Ru(IV), Ti(III), Cr(IV), Bi(III), Ni(II), W(V), W(IV), Mo(II), Mo(III), Mo(IV), Mo(V), Mo(VI), or a combination of two or more thereof. The Roman numerals in the foregoing indicate oxidation states or valence numbers for the ions.

The ligands that may be used to complex the metal ions include dipyridyl; 2,6-[1-(2-imidazol-4-ylethylimino)ethyl pyridine]; cyclen; cyclam; a Schiff base ligand; acetyl acetonate or an oligomer or polymer thereof; a carboxylate; bipyridyl or an oligomer or polymer thereof; a porphyrin or an oligomer or polymer thereof; a corin or an oligomer or polymer thereof; a polyamide; a protein; 8-hydroxy quinoline or an oligomer or polymer thereof; ethyl cysteinate or an oligomer or polymer thereof; an N-alkyl alkanohydroxamic acid; dimethylglyoxime; sym-diethylethylenediamine; or a combination of two or more thereof. The ligands may include fluoride-carbon bonds. The ligands may be fluorinated (e.g., perfluourinated).

In one embodiment, the metal-ion ligand complex may be an axial ligand. These ligands may be suitable for oxygen purification because they tend to provide suitable bonds with oxygen to allow adduct formation, but not oxidation of the metal. Examples include imidazole, histidine amino acid, pyridine, piperidine, 4-methyl aminopyridine, 4-dimethyl aminopyridine, a nitrate, a thiocyanate, a halide, or a combination of two or more thereof.

The sorption medium that may be used may be hemoglobin; hemoerythyrin; hemocyanin; myoglobin; Co(II) (acacen); Co(II) (dry cave) (N-methyl imidazole); Fe(II) (H2TpivPP)B; Fe(II)(capped porphyrin)B; Fe(ophen)$_2^{2+}$; bis(ethyl cysteinato) oxovanadium (IV); Cu(I) (bimp); bis (dimethylglyoximato)cobalt(II); bis(histidine)cobalt(II); dinitrato-bis(sym-diethylethylenediamine)cobalt(II); dichloro-bis(sym-diethylethylenediamine)cobalt(II); [m-tetra(a,a,a,a-o-pivalamidophenyl)porphyrin]cobalt(II); [N,N-bis(salicylidene)dipropylenetriamine]cobalt(II); [2,3,10,11,13,19-hexamethyl-3,10,14,18,21,25-hexaazabicyclo [10.7.7]hexacosa-1,11,13,18,20,25-hexene-k$^4$N)cobalt(II) hexafluorophosphate; [N,N'-bis(salicylicylidene) ethylenediamine]cobalt(II); [N,N'-bis(3-methoxysalicylicylidene)ethylenediamine]cobalt(II); [N,N'-bis(salicylicylidene)tetramethylethylenediamine]cobalt(II); [N,N'-bis(3-methoxysalicylicylidene)tetramethylethylene-diamine]cobalt(II); [N,N'-bis(3-isoprpoxysalicylicylidene) tetramethylethylenediamine]cobalt(II); [N,N'-bis(3-ethoxysalicylicylidene)tetramethylethylenediamine]cobalt(II); [N,N'-bis(5-methoxysalicylicylidene)tetramethylethylene-diamine]cobalt(II); [N,N'-bis(5-n-butoxysalicylicylidene) tetramethylethylenediamine]cobalt(II); [N,N'-bis(salicylidene)ethylenediamine]cobalt(II)); a cobalt(II)porphyrin complex; a metal-cyanide complex encapsulated within a zeolite; a cyanocobaltate; hemoglobin, hemerythrin or hemocyanin containing a diiron(III,IV), dicopper(II) or dimanganese core; N,N'-disalicylideneethylenediamine cobalt(II); cobalt di-(3-methoxysalicylal tertbutylamine); [N,N'-bis(salicylidene)n-propyldipropylenetriamine]cobalt (II); 1-methylimidazole; 2-methylimidazole; 4-dimethylaminopyridine; cyanopyridine; cobalt chelated copolymer derived from ethylene-diamine-tetraacetic acid, methyl methacrylate and butyl acrylate; bis(histidine) cobalt(II); [a-mono(o-methacrylamidophenyl)-a,a,a-tris(o-pivalamidophenyl)porphinato]cobalt; [meso-a,a,a,a-tetrakis(o-pivalamidophenyl)porphinato]-iron(II); cobalt(II) meso-tetra-phenyl-porphyrin; cobalt(II) meso-tetrakis(2-chlorophenyl) prophyrin; cobalt(II) meso-tetrakis(4-chlorophenyl) porphyrin; cobalt(II) meso-tetrakis(4-methoxy phenyl) porphyrin; cobalt(II) meso-tetrakis(2,4-dimethoxy phenyl) porphyrin; ruthenium (III) bis(salicylaldehyde) ethylenediimine; ruthenium (III) bis(salicylaldehyde) diethlenetriimine; ruthenium (III) bis(picolinaldehyde)-o-phenylenediimine; ruthenium (III) bis(picolinaldehyde) ethylenediimine; ruthenium (III) bis(picolinaldehyde) diethylenetriimine; bis(dimethylglyoximato)nickel(III); bis (dimethylglyoximato)cobalt(II); bis(dimethylglyoximato) copper(III); dinitrato-bis(sym-diethylenediamine)cobalt(II); dithiocyanato-bis(sym-diethylethelenediamine)cobalt(II); dichloro-bis(sym-diethylethylenediamine)cobalt(II); cobalt di-(salicylal)-3,3'-diimino-di-n-propylamine; N,N'-disalicyclidene ethylene diamine cobalt (II); N,N'-ethylene-bis(5-nitro-salicyliden-iminato) cobalt(II), or a combination of two or more thereof.

The sorption medium may be inorganic. Examples of inorganic sorption mediums that may be used include $Sb_2O_5$, AgO, PtO, $CrO_2$, PbO, HgO, $Cu_2O$, MnO, $Mn_2O_3$, $Bi_2O_4$, NiO, $NiO_2$, $Cu_2O_3$, SnO, $SnO_2$, $WO_2$, $WO_3$, $W_2O_5$, perfluororinated film, Pt/g-alumina, Fe/g-alumina, Cu/g-alumina, Zn/g-alumina, Co/g-alumina, zeolite, or a combination of two or more thereof. Included in this group are metal cyanide oligomers and polymers. These include the oligomers and polymers represented by the formulae $[Cu(I)(CN)_x]_n$, $[Fe(II)(CN)_y]_n$, or $[Co(II)(CN)_y]_n$, wherein x is 3; y is 5; and n is a number that is at least 2, and in one embodiment is in the range of about 2 to about 16,500, and in one embodiment about 1000 to about 10,000.

The sorption medium may comprise silver, gold, platinum, copper, zinc, palladium, nickel, zeolite, silica gel, carbon molecular sieves, polymeric materials, alumina, inorganic complexes (e.g., metal centered porphyrin rings) or a combination of two or more thereof.

In one embodiment, the sorption medium comprises a reactive complexation sorbent that forms a reversible chemical complex with a fluid component at a relatively high temperature wherein the fluid component is sorbed by the surface of the sorption medium. At a lower temperature the chemical reaction is reversed and the complexed fluid is recovered in a more purified form.

The sorption medium may comprise an antioxidant. Examples include secondary amines, phenolic phosphates, phosphites, phenolics, bisphenolics, hydroxylamines, olefinic carboxylates, amino carboxylates (e.g., ethylene diamine tetracetic acid and salts thereof), tocopherol, di-tertiarybutyl-p-cresol, stannous salts, stannous oxides, sorbate, polysorbate, or a combination of two or more thereof.

An advantage of the invention is that the use of a fin structure to support an active sorption medium enables a relatively fast thermal swing. A metallic fin structure may have a thermal conductivity in the range of about 10 to about 20 W/m/K or greater depending on the material selected. Aluminum may exceed 100 W/m/K. On the other hand, the thermal conductivity of a porous medium such as a pellet or powder sorbent bed is typically in the range of about 0.2 to about 2 W/m/K. As a result, the use of a fin supported sorption medium enables faster cycle times due to enhanced heat transfer through the fin versus a porous medium. The difference in cycle time is roughly proportional to the difference in thermal conductivity of the sorption medium. The use of a fin supported sorption medium permits the time for each cycle to be reduced significantly as compared to a porous sorption medium. This enhancement in cycle times facilitates both gas phase and liquid phase sorption separation processes.

EXAMPLE 1

A steam/methane reforming (SMR) process with integrated combustion on the opposing side of the heat transfer plane is conducted in a microchannel reactor employing an FeCrAlY fin supported SMR catalyst. The use of an SMR catalyst on fins inserted in a process microchannel produces surprisingly high heat fluxes (10 to 141 W/cm$^2$, low SMR contact times (10 to 0.7 ms), and low SMR pressure drops.

Except for the FeCrAlY fin which supports the SMR catalyst, the microchannel reactor is constructed of Inconel 617 plates of various thicknesses which are stacked, clamped together, and welded at the perimeter to form a reactor 0.5 by 3.63 inch (12.7 by 92 mm) in footprint by 0.67 inch (17.1 mm) high. All channels for gas flow are machined using conventional techniques except air jet orifices, which are formed via electrode discharge machining (EDM). An air header plate (6.35 mm thick with a 12.7 by 56.5 mm footprint) is welded in a 2.54 mm deep pocket machined into a combustion plate over the air jet orifices. On the face adjacent to the combustion plate is machined an air header channel of dimensions 0.125 inch (3.18 mm) deep by 0.080 inch (2.03 mm) wide by 1.84 inches (46.8 mm) in length. The combustion plate is stacked next to a web plate, which is stacked next to an SMR plate. The SMR plate is divided into three sections which lie in the same plane and are each welded together and to the web plate after stacking. Along the entire 56.7 mm length of the center SMR section (which is centered between 17.7 mm long header and footer sections) is machined a fin-containing microchannel. The adjacent SMR plate sections each have formed therein a header or footer channel of 2.03 by 0.66 mm cross section and 12.6 mm in length. The combustion plate is machined on the face adjacent to the web plate to form a 1.78 inch (4.52 cm) long combustion channel, to provide heat to the endothermic SMR reaction. The combustion channel has a cross section of 0.080 by 0.036 inch (2.03 by 0.91 mm). The combustion plate also contains jet orifices centered on the combustion channel centerline along the direction of flow, machined by electrode discharge machining (EDM) through a 0.150 inch (3.81 mm) plate thickness, thereby connecting the air header channel to the combustion channel. Combustion flows are fed co-flow with respect to the SMR gases. The combustion channel is fed hydrogen at the inlet to the combustion channel and pre-heated air is introduced the aforementioned airjet orifices distributed over the 45.2 cm length of the combustion zone, specifically at 1.0, 2.7.4.8, 7.4, 14.7, 24.4, and 34.0 mm downstream from the combustion zone inlet. The cross section of the airjet orifice at 1.0 mm and 4.8 mm axial location are oblong along the axis of flow with dimensions of 0.024 by 0.012 inch (0.61 by 0.30 mm) with full rounds at both ends. The cross section of the jet hole at 2.7 mm axial location is an equilateral triangle which "points" downstream, having sides of 0.024 inch (0.61 mm) and 0.05 mm radius rounds on the corners. All other air jet orifices are circular in cross section, with a diameter of 0.012 inch (0.30 mm). The hydrogen fuel is brought to the combustion zone in a 23.4 mm long header region with a 2.03 by 0.41 mm cross section. At the end of the combustion fuel header the 0.41 mm dimension opens up to 0.91 mm in a sudden expansion away from the web and toward the jet holes. Separating the combustion channel and SMR reaction process microchannel is a 0.060 inch (1.52 mm) web, solid except for the 0.023 inch (0.58 mm) diameter thermowells which are drilled 0.25 inch (6.35 mm) deep from the perimeter to the center of the web plate (which is also the center of the microchannel width). These thermowells, placed in the web at six locations along the length of the reaction zone, allow temperature measurement in the metal between the SMR and combustion channels via 0.50 mm type K ungrounded Inconel sheathed thermocouples without compromising the gas-tight seal on either the combustion or SMR channels. Gases are introduced into the air, hydrogen, and SMR reactant inlets and removed from the combustion exhaust and SMR product outlets via 1.75 mm inside diameter (3.18 mm OD) tubes which extend orthogonal to the plane of each plates. An additional four 1.75 mm ID tubes provided access to the SMR channel at both ends of the fin and to the combustion channel at levels corresponding to the beginning and end of the combustion zone.

The FeCrAlY fin inserted into the microchannel is 1.78 inches (4.52 cm) in length and 0.100 inch or 2.54 mm wide at the base. The base has a height of 0.006 inch or 0.152 mm. Each fin is 0.014 inch tall and sits on top of the 0.006 inch base. Each fin is spaced 0.010 inch apart from the adjacent fin to create a gap for flow of 0.010 inches. There are 4 fins protruding up from the fin support. The fin support sits on top of the heat transfer plane that separates the SMR reaction process microchannel and the adjacent heat exchange combustion reaction chamber.

The cross-section of the microchannel containing the fin insert is 0.080 inch (2.03 mm) (extending to 0.100 inch (2.54 mm) at the fin base) by 0.026 inch (0.66 mm). The microchannel reactor fin has a length of 1.78 inches (4.52 cm)

containing an SMR catalyst washcoated on a FeCrAlY fin insert. The fin is inserted into the microchannel reactor before welding the reactor, along with two small Inconel pieces (0.18 by 2.54 by 5.74 mm) at either end of the fin which hold it centered lengthwise in the channel and prevent flow in the plane of the fin base immediately upstream and downsteam of the fin.

Before inserting the FeCrAlY fin into the process microchannel, the fin is cleaned using 2-propanol, $HNO_3$ (20 wt %), and deionized water by ultrasonic cleaner 10 min each. Then, it is heat treated in air at 1000° C. for 8 hrs with a heating and cooling rate of 3.5° C./min before placing into the process microchannel and welding the device at the perimeter.

Before coating the FeCrAlY fin with catalyst, an oxide layer is grown on the FeCrAlY fin by flowing 200 standard cubic centimeters (sccm) nitrogen through each of the inlet tubes (air, fuel, SMR reactant) while heating to 1000° C. at 3.5° C. per minute. The nitrogen flow is then stopped and 200 sccm of hydrocarbon free air is fed through the three inlets for 24 hours at 1000° C. The device is then cooled to 25° C. at a rate of 3.5° C. per minute (maintaining continuous air flow), and placed in the process microchannel. The device is welded at the perimeter.

Using external washcoat holes, the SMR and combustion reactant channels are wash-coated with stabilizer and active metal only in the regions corresponding to the SMR finned substrate. An alumina sol coating is applied to the entire reactor, including inlet and outlet tubing, to help prevent background activity.

Alumina sol (14N4-25 supplied by Sasol) is introduced to the combustion and SMR channels using a syringe to fill the channels and inlet/outlet tubing from the bottom with the channels oriented vertically. The device is allowed to soak for 2 minutes before the sol is removed from the channels. Nitrogen is fed at 5 standard liters per minute (SLPM, standard defined as 0° C. and 1 atmosphere) to remove excess sol. The device is dried in a furnace at 100° C. for 1 hour with hydrocarbon free air flowing at 150 cc/min followed by calcination at 450° C. for 4 hours at a heating and cooling rate of 10° C./min. A second layer of sol is then applied to the combustion and SMR channels in the same method described for the first layer of sol coating. A 10% by weight aqueous solution of $La(NO_3)_3 \cdot 6H_2O$ is introduced continuously to the combustion channel using a syringe pump at a rate of 60 ml/hr. For this step and subsequent steps, the solution is continuously introduced through a washcoat tube at one end of the reaction zone and removed through a washcoat tube at the other end of the process zone with the channels in a horizontal orientation. During this coating step 20 sccm nitrogen are introduced through the inlet and outlet tubing to prevent impregnation of the inlet and outlet regions. Afterward the solution is removed from the channel and the device is flushed with nitrogen to remove excess solution. The same procedure is repeated to coat the SMR channel with the aqueous solution o La $(NO_3)_3 \cdot 6H_2O$. After the SMR channel is flushed with nitrogen, it is dried at 100° C. for 1 hour in hydrocarbon free air at 150 cc/min. Then it is calcined at 1000° C. for 4 hours with a heating and cooling rate of 3.5° C./min.

The combustion channel is coated with first layer of active metals consisting of praseodymium and palladium at 4 to 1 atomic ratio using precursors in the form of nitrate. The solution is introduced into the combustion channel and then removed in the same way as previously described for the La step. The device is dried at 100° C. for 1 hour with hydrocarbon free air flowing at 150 cc/min, followed by calcination at 1000° C. for 1 hour with a heating and cooling rate of 10° C./min.

The second layer of active metal consisting of platinum is coated in the combustion channel with 10% by weight $Pt(NH_3)_4(NO_3)_2$ using the syringe pump. The solution is introduced into the combustion channel and then removed in the same way as previously described for the La step. Then, the SMR channel is coated with a second active metal layer consisting of 10% by weight rhodium in nitrate solution using the syringe pump. The solution is introduced into the SMR channel and then removed in the same way as previously described for the La step. The device is dried at 100° C. for 1 hour with hydrocarbon free air flowing at 150 cc/min, followed by clacination at 1000° C. for 1 hr with a heating and cooling rate of 3.5° C./min.

The entire reactor is operated inside a 15 cm clamshell Ni—Cr ceramic heater which is held at a temperature about 25–50° C. below the maximum combustion web temperature to offset the effect of thermal losses. Preheat is provided to the reactant and air streams via external heaters.

Each reactant gas is fed via Brooks 5850e and 5851e series mass flow controllers. Pressure is measured using NoShok pressure transducers model 1001501127 and 1003001127. Gas compositions are analyzed via a thermal conductivity detector gas chromatograph. All equipment is calibrated and verified for proper operation. Flow rates are calibrated against a primary standard calibrator, the Dry-Cal DC-2M Primary Flow Calibrator, which is calibrated and certified by BIOS International. Pressure transducers are calibrated using a Fluke pressure calibrator model 718 1006 with a Fluke 700P07 or 700P06 pressure module which are calibrated and certified by Fluke. The gas chromatograph is calibrated against calibration gases blended and certified by Praxair Distribution Inc. Neat hydrogen is used as the combustion fuel and 5–27% excess air is used. Combustion exhaust analysis consistently show 100% hydrogen conversion.

"Average area heat flux" is defined as the endothermic reaction heat duty divided by the planar area of the heat transfer surface adjacent to the base of the fin. This area is the path for heat transfer from the heat exchange channel to the base of the fin.

"Web" is defined as the wall that separates the endothermic reaction (fin containing) process microchannels and the heat exchange combustion reaction chamber.

"Equilibrium conversion temperature" (Table 1) is the temperature required for the given inlet composition to produce an equilibrium methane conversion equal to the measured methane conversion at the measured process outlet pressure. Similarly, the "equilibrium selectivity temperature" (Table 1) is the temperature required for the given inlet composition to produce an equilibrium selectivity to CO value equal to the measured selectivity to CO at the measured process outlet pressure. Equilibrium gas compositions are calculated using the NASA LEWIS thermodynamic equilibrium code or ChemCAD. Methane conversion and selectivity to carbon monoxide are calculated from the dry product gas composition as measured by gas chromatograph according to Equations 1 and 2

$$CH_4 \text{ Conversion} = 1 - (Y_{CH4}/Y_{CH4} + Y_{CO} + Y_{CO2}) \quad (1)$$

$$\text{Selectively to CO} = Y_{CO}/(Y_{CO} + Y_{CO2}) \quad (2)$$

where Y is the mole fraction of each indicated component.

The contact time (CT) is the inverse of the gaseous hourly space velocity (GHSV), multiplied by a conversion factor to convert inverse hours into milliseconds:

$$CT = (1/GHSV)(3600000 \text{ ms/hr})$$

where GHSV is the space velocity in inverse hours. The rate of volumetric flow rate fed to the reactor is defined at the standard condition of 0° C. and 1 atmosphere of pressure for the purposes of calculating either contact time or GHSV. Thus the contact time and GHSV depend only on the inlet molar flowrate and the reaction chamber volume.

Figure 13:
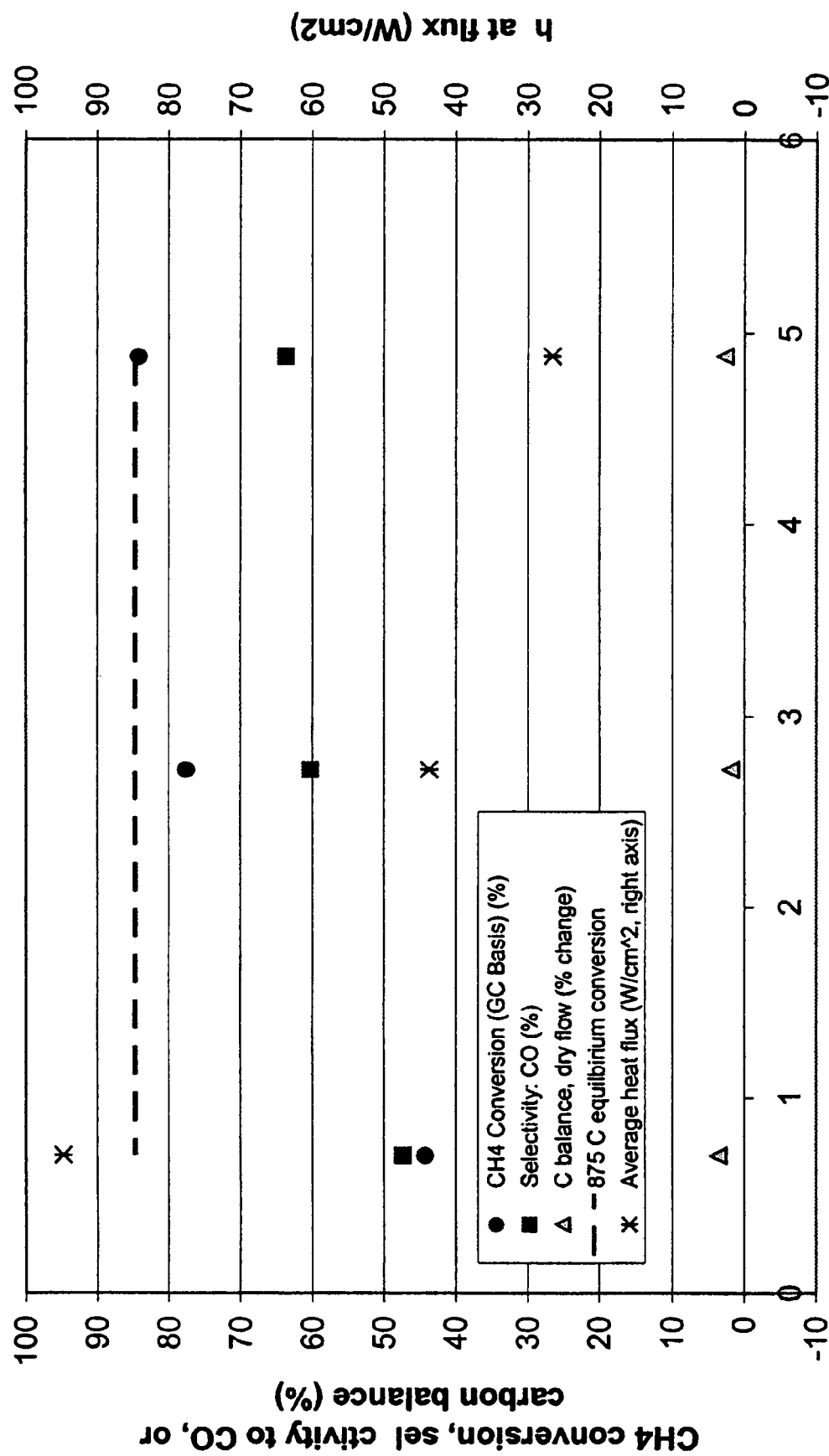
FIGS. 13 and 14 are graphs disclosing results obtained in Example 1.
Figure 14:
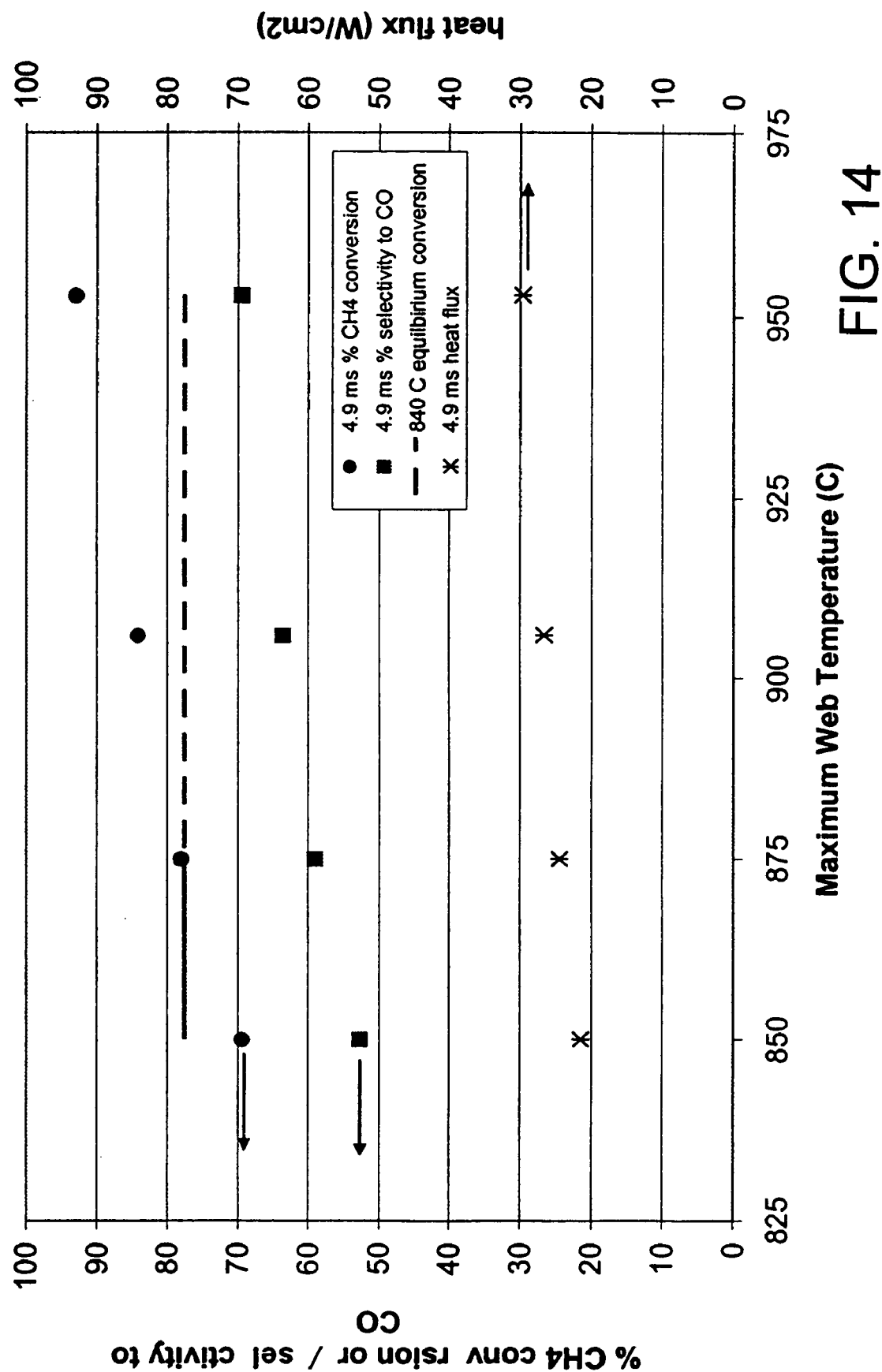

The performance data for the reactor is shown in Table 1 and FIGS. 13 and 14. For maximum metal web temperatures of 950 and 900° C., equilibrium SMR conversion and selectivity are achieved at an apparent SMR temperatures of 925 and 875° C., respectively and heat fluxes of >25 W/cm² at a contact time of less than 5 milliseconds (ms). For faster contact times, fluxes up to 90–140 W/cm2 are achieved, showing the ability of the SMR fin supported catalyst to keep up with the higher heat demand at the upstream section of the catalyst. Data taken at 14 atmospheres with a combustion metal web temperature of 875° C. show ~800° C. equivalent conversion, although the same temperature condition at 25 atm shows ~840° C. equivalent conversion.

The fin supported SMR process microchannel is used to test the maximum heat flux achievable at the upstream end of the SMR reactor. At a total flow rate of 7.4 standard liters per minute (SLPM) of reactant (0.5 ms contact time in the 1.78 inch catalyst bed), 25 atm, and maintaining a maximum combustion web temperature of 950° C., an average heat flux exceeding 140 W/cm2 is achieved, giving conversion and selectivity values equivalent to about 700 and 800° C. equilibrium values, respectively (see Table 1).

TABLE 1

| Condition (Temperature and Contact Time) | 950° C. 5.0 ms | 900° C. 2.7 ms | 950° C. 2.7 ms | 900° C. 0.7 ms | 950° C. 0.7 ms |
|---|---|---|---|---|---|
| Time on stream (hr) | 75 | 25 | 20 | 92 | 72.5 |
| Contact time (ms) | 4.9 | 2.7 | 2.7 | 0.7 | 0.7 |
| Maximum web temperature (° C.) | 953 | 906 | 953 | 900 | 950 |
| Average area heat flux (W/cm²) | 29.7 | 43.7 | 50.8 | 94.7 | 141.9 |
| Equilibrium conversion temp. (° C.) | 935 | 840 | 902 | 701 | 708 |
| Equilibrium selectivity temp. (° C.) | 924 | 846 | 901 | 776 | 792 |
| Air inlet gas temperature (° C.) | 932 | 880 | 930 | 856 | 887 |
| Exhaust gas temperature (° C.) | 940 | 884 | 938 | 872 | 917 |
| Air inlet pressure (kPa) | 124 | 123 | 127 | 148 | 190 |
| Total fuel flow rate (SLPM) | 0.152 | 0.184 | 0.222 | 0.454 | 0.693 |
| Fuel $H_2$ content (%) | 100 | 100 | 100 | 100 | 100 |
| Air flow rate (SLPM) | 0.460 | 0.460 | 0.554 | 1.135 | 2.095 |
| % excess air (based on inlet flows) | 27 | 5 | 5 | 5 | 27 |
| Air pressure drop (kPa) | 9.7 | 9.0 | 11.7 | 26.9 | 58.6 |
| SMR inlet gas temperature (° C.) | 915 | 860 | 906 | 810 | 814 |
| SMR outlet gas temperature (° C.) | 940 | 879 | 934 | 847 | 874 |
| SMR inlet pressure (kPa) | 2560 ± 5 | 2560 ± 5 | 2570 ± 5 | 2600 ± 5 | 2630 ± 5 |
| SMR outlet pressure (kPa) | 2560 ± 5 | 2560 ± 5 | 2570 ± 5 | 2570 ± 5 | 2560 ± 5 |
| SMR $CH_4$ flow rate (SLPM) | 0.182 | 0.326 | 0.326 | 1.264 | 1.82 |
| SMR steam flow rate (SLPM) | 0.547 | 0.980 | 0.980 | 3.78 | 5.46 |
| Molar steam to methane Ratio | 3.0 | 3.0 | 3.0 | 3.0 | 3.0 |
| $CH_4$ conversion (GC Basis) (%) | 93.0 | 77.6 | 89.1 | 44.3 | 45.7 |
| Selectivity: CO (%) | 69.5 | 60.2 | 67.4 | 47.3 | 50.6 |
| SMR (carbon out)/(carbon in) | 1.05 | 1.02 | 1.03 | 1.04 | 0.98 |
| Web temperature 1.0 mm from catalyst fin upstream end (° C.) | 953 | 906 | 953 | 900 | 950 |
| Web temperature 2.8 mm from catalyst fin upstream end (° C.) | 948 | 906 | 953 | 898 | 944 |
| Web temperature 5.4 mm from catalyst fin upstream end (° C.) | 943 | 901 | 949 | 888 | 930 |
| Web temperature 17.2 mm from catalyst fin upstream end (° C.) | 930 | 895 | 940 | 878 | 912 |
| Web temperature 28.0 mm from catalyst fin upstream end (° C.) | 929 | 886 | 933 | 864 | 893 |
| Web temperature 39.2 mm from catalyst fin upstream end (° C.) | 943 | 888 | 940 | 866 | 897 |
| Furnace temperature (° C.) | 935 | 883 | 934 | 864 | 902 |

EXAMPLE 2

Fins for use in a partial oxidation reaction process are designed and tested for methane partial oxidation to synthesis gas with focus on following characteristics:
1. High $CH_4$ conversion: use of the fin should provide high $CH_4$ conversion.
2. High $H_2$ Selectivity: use of the fin should provide high $H_2$ selectivity.
3. High CO Selectivity: use of the fin should provide high CO selectivity.
4. Low Pressure Drop: use of the fin should offer low resistance to flow.
5. Mechanical and thermal strength: The fin should have high mechanical strength to sustain large stress conditions inside the channel during fabrication of the device (like bonding) and its operation. A design with good heat transfer characteristics prevents hot spots and material degradation.

FIG. 6 shows the geometry of a fin that is useful for conducting a POX reaction process in a combustion microchannel. The trapezoidal shape of the fins provides mechanical rigidity at the base of fins. All the fins are supported on rectangular base to enhance heat transfer characteristics of the fin. The fin is fabricated from FeCrAlY using the Wire EDM method. The following table summarizes dimensions of the fin:

|  | Dimension (in) |
|---|---|
| Fin thickness | |
| At base | 0.005 |
| At top | 0.002 |
| Fin spacing | |
| At base | 0.012 |
| At top | 0.017 |
| Fin height | 0.029 |
| Rectangular base height | 0.020 |
| Overall width | 0.180 |
| Overall Height | 0.049 |
| Overall length | 1.500 |

An $Al_2O_3$ slurry is prepared by mixing 7.2 g of gamma $Al_2O_3$ powder, 12 g of deionized $H_2O$ and 42 g $Al_2O_3$ beads with 3 mm diameter. The pH value is adjusted to 3.5–4 using nitric acid. The $Al_2O_3$ is acidic gamma $Al_2O_3$ which is ground to powder smaller than 150 micrometers. The mixture is ball-milled for 8 hours. 0.8 g of 25 wt. % $Al_2O_3$ sol (Sasol 14N4-25) is added to 4.2 g of the slurry with stirring.

The FeCrAlY fin is cleaned in iso-propanol for 20 min with sonication. After drying at 100° C. for 1 h and cooling to room temperature, the fin is cleaned in 20 wt. % $HNO_3$ solution for 20 min with sonication. The fin is then rinsed with deionized water until the pH value is 7. After drying at 120° C. for 1 hour, the fin is heated to 1000° C. in air at a heating rate of 3.5° C./min and calcined at 1000° C. for 8 hours in air. A dense $Al_2O_3$ layer is generated after the calcination. The $Al_2O_3$ layer functions as a protection scale and also improves the adhesion between the coating and the fin. The $Al_2O_3$ slurry is washcoated onto the fin by dipping. The excess slurry is removed by jetting air over the coated surface. The fin is dried at 120° C. for 1 hour and then calcined at 450° C. for 4 hours at a heating and cooling rate of 3.5° C./min. A 7.5 wt. % $La(NO_3)_3$ solution is impregnated onto the fin by dipping. The fin is dried at 120° C. for 1 hour and then calcined at 1000° C. for 4 hours in air at a heating and cooling rate of 3.5° C./min. The $La_2O_3$ on the surface stabilizes the $Al_2O_3$. The slurry loading is 25.4 mg per fin. A 10 wt. % $Rh(NO_3)_3$ solution is dropped onto the fin and the excess solution is blown out by compressed air. The resulting fin supported catalyst is dried at 120° C. for 1 hour and then calcined at 1000° C. for 1 h in air. The Rh loading is 4.8 mg per fin.

The fin supported catalyst is tested for partial oxidation of methane to syngas at 1 atmosphere in a pellet. The pellet is a cylindrical metal rod having a diameter of 0.5 inch and a length of 2 inches. The pellet has a rectangular microchannel cut-away in its center. The cut-away extends through the rod along its interior axis. The cut-away has a height of 0.05 inch and a width of 0.18 inch. The fin supported catalyst is placed in the cut-away for testing. Gas tight connections are made on each side of the cut-away. The reactants flow through tubing to the cut-away, and through the cut-away in contact with the fin supported catalyst. The pellet is placed in a furnace. The temperature of the furnace is increased to keep the pellet outside skin temperature at mid-length at 850° C. The temperature of the feed stream at the inlet of the furnace is at room temperature and is preheated before entering the pellet. The length of the tubing from the entrance of the furnace to the pellet is 10 feet. The outlet pressure of the product stream is atmospheric pressure. The pressure drop in the pellet is measured using a Capsuhelic differential pressure gauge. The composition of the product is analyzed with a two-column Gas Chromatograph. The performance of the fin supported catalyst is measured in terms of $CH_4$ conversion, $H_2$ selectivity and CO selectivity.

$CH_4$ Conversion (%)=$(V_{CH4}, in - V_{CH4}, out)/(V_{CH4}, in) \times 100$ $H_2$ Selectivity (%)=$(V_{H2}, out, actual)/(V_{H2}, out, theoretical) \times 100$ CO Selectivity (%)=$(V_{CO}, out)/(V_{CO}, out + V_{CO2}, out) \times 100$ The catalyst is reduced with $H_2$ at 400° C. for 30 min before use. The feed gas compositions are 29.6% of $CH_4$ and 70.4% of air ($CH_4/O_2=2/1$), with 2030 ml/min of total flow rate (standard conditions). The contact time is 3.3 ms. The contact time is defined as the ratio of flow volume in the pellet without the fin to the volumetric flow rate. The following table summarizes the fin supported catalyst performance after 157 hours of operation.

| Parameter | Value |
|---|---|
| Coating Type | Powder slurry wash-coat |
| Fuel composition | 29.6% $CH_4$, 70.4% air |
| Fuel contact time | 3.3 ms |
| $CH_4$ Conversion (at 850° C.) | 85% |
| $H_2$ Selectivity (at 850° C.) | 92% |
| CO Selectivity (at 850° C.) | 95% |
| Pressure drop | 5.6 psi |

EXAMPLE 3

An alternate fin for use in a POX reaction process provides the advantage of reduced pressure drop. The flow area is increased by reducing number of fins. There are five fins projecting up from the fin support. The fins have a trapezoidal cross section as indicated in FIG. 6. The thickness of the fin along with trapezoidal shape of the fins provides mechanical rigidity at the base of the fins. The fins are supported on rectangular support or base to enhance heat transfer characteristics of the fin. The fin is made from FeCrAlY. The fin is fabricated by the wire EDM method. The following table summarizes dimensions of the fin:

|  | Dimension (in) |
| --- | --- |
| Fin Thickness |  |
| At base | 0.020" |
| At top | 0.010" |
| Fin spacing |  |
| At base | 0.012" |
| At top | 0.022" |
| Fin height | 0.033" |
| Rectangular base height | 0.020" |
| Overall width | 0.180" |
| Overall height | 0.053" |
| Overall length | 1.500" |

An $Al_2O_3$ slurry is prepared by mixing 7.2 g of gamma $Al_2O_3$ powder, 12 g of deionized $H_2O$ and 42 g $Al_2O_3$ beads with 3 mm diameter. The pH value is adjusted to 3.5–4 using nitric acid. The $Al_2O_3$ is acidic gamma $Al_2O_3$ and is ground to powder smaller than 150 micrometers. The mixture is then ball-milled for 8 hours. 0.8 g of 25 wt. % $Al_2O_3$ sol (Sasol 14N4-25) is added to 4.2 g of the slurry with stirring.

The FeCrAlY fin is cleaned in iso-propanol for 20 min with sonication. After drying at 100° C. for 1 hour and cooling to room temperature, the fin is cleaned in 20 wt. % $HNO_3$ solution for 20 min with sonication. The fin is rinsed with deionized water until the pH value is 7. After drying at 120° C. for 1 hour, the fin is heated to 1000° C. in air at a heating rate of 3.5° C./min and calcined at 1000° C. for 8 hours in air. The $Al_2O_3$ slurry is washcoated onto the fin by dipping. The excess slurry is removed by jetting air over the coated surface. The fin is dried at 120° C. for 1 hour and then calcined at 450° C. for 4 hours at a heating and cooling rate of 3.5° C./min. A 7.5 wt. % $La(NO_3)_3$ solution is impregnated onto the slurry-coated fin by dipping. The fin is dried at 120° C. for 1 hour and calcined at 1000° C. for 4 hours in air at a heating and cooling rate of 3.5° C./min. The slurry loading is 6.0 mg per fin. A 10 wt. % $Rh(NO_3)_3$ solution is dropped onto the fin and the excess solution is blown out by compressed air. The fin is dried at 120° C. for 1 hour and then calcined at 1000° C. for 1 hour in air. The Rh loading is 1.0 mg per fin.

The resulting fin supported catalyst is tested for partial oxidation of methane to syngas at 1 atmosphere in the pellet described in Example 2. The pellet is placed in a furnace. The temperature of the furnace is adjusted to keep the pellet skin temperature at mid-length at 805° C. The temperature of the feed stream at the inlet of furnace is at room temperature. The feed stream is preheated before entering the pellet. The length of tubing from the entrance of furnace to the pellet is 10 feet. The outlet pressure of the product stream is atmospheric pressure. The pressure drop in the pellet is the difference between the inlet and the outlet pressures. The composition of product is analyzed with a two-column Gas Chromatograph. The performance of the fin is measured in terms of $CH_4$ conversion, $H_2$ selectivity and CO selectivity. The following table summarizes catalyst performance for the fin after 115 hours of operation.

| Parameter | Value |
| --- | --- |
| Coating Type | Powder slurry wash-coat |
| Fuel composition | 29.6% $CH_4$, 70.4% air |
| Fuel contact time | 3.3 ms |
| $CH_4$ Conversion (at 850° C.) | 78% |
| $H_2$ Selectivity (at 850° C.) | 93% |
| CO Selectivity (at 850° C.) | 93% |
| Pressure drop | 2.8 psi |

EXAMPLE 4

An FeCrAlY fin is fabricated with saw-cut method and tested in a pellet for catalyst performance. The following table summarizes dimensions of the fin:

|  | Dimension (in) |
| --- | --- |
| Fin Thickness |  |
| At base | 0.010" |
| At top | 0.005" |
| Fin spacing |  |
| At base | 0.017" |
| At top | 0.022" |
| Fin height | 0.033" |
| Rectangular base height | 0.020" |
| Overall width | 0.180" |
| Overall height | 0.053" |
| Overall length | 1.500" |

An $Al_2O_3$ slurry is prepared by mixing 7.2 g of gamma $Al_2O_3$ powder, 12 g of deionized $H_2O$ and 42 g $Al_2O_3$ beads with 3 mm diameter. The pH value was adjusted to 3.5–4 using nitric acid. The $Al_2O_3$ is acidic gamma $Al_2O_3$, is ground to powder smaller than 150 micrometers. The mixture is then ball-milled for 8 hours. 0.8 g of 25 wt. % $Al_2O_3$ sol (Sasol 14N4-25) is added to 4.2 g of the slurry with stirring.

The FeCrAlY fin is cleaned in iso-propanol for 20 min with sonication. After drying at 100° C. for 1 hour and cooling to room temperature, the fin is cleaned in 20 wt. % $HNO_3$ solution for 20 min with sonication. The fin is then rinsed with deionized water until pH value reaches 7. After drying at 120° C. for 1 hour, the fin is heated to 1000° C. in air at a heating rate of 3.5° C./min and calcined at 1000° C. for 8 hours in air. The $Al_2O_3$ slurry is washcoated onto the fin by dipping. The excess slurry is removed by jetting air over the coated surface. The fin is dried at 120° C. for 1 hour and then calcined at 450° C. for 4 hours at a heating and cooling rate of 3.5° C./min. 7.5 wt. % $La(NO_3)_3$ solution is impregnated onto the slurry-coated fin by dipping. The fin is dried at 120° C. for 1 hour and calcined at 1000° C. for 4 hours in air at a heating and cooling rate of 3.5° C./min. The slurry loading is 18.7 mg per fin. 10 wt. % $Rh(NO_3)_3$ solution is dropped onto the fin and the excess solution is blown out by compressed air. The fin is dried at 120° C. for 1 hour and calcined at 1000° C. for 4 hours in air. The Rh loading is 3.2 mg per fin.

The resulting fin supported catalyst is tested for partial oxidation of methane at 1 atmosphere in the pellet described in Example 2. The pellet is placed in a furnace. The catalyst is reduced with $H_2$ at 400° C. for 30 min before use. The feed gas compositions are 29.6% of $CH_4$ and 70.4% of air ($CH_4/O_2$=2/1), with 2372 ml/min of total flow rate (standard conditions). The contact time is 3.3. The temperature of the furnace is adjusted to keep the pellet skin temperature at mid-length at 850° C. The temperature of the feed stream at the inlet of furnace is at room temperature. The feed stream is preheated before entering pellet. The length of tubing from the entrance of furnace to the pellet is 10 feet. The outlet pressure of the product stream is atmospheric pressure. The pressure drop in the pellet is measured by a capsuhelic differential pressure gauge. The composition of product is analyzed with a two-column Gas Chromatograph. The performance of the fin is measured in terms of $CH_4$ conversion, $H_2$ selectivity and CO selectivity. The following table summarizes the fin supported catalyst performance after 400 hours of operation.

| Parameter | Value |
| --- | --- |
| Coating Type | Powder slurry wash-coat |
| Fuel composition | 29.6% $CH_4$, 70.4% air |
| Fuel contact time | 3.3 ms |
| $CH_4$ Conversion (at 850° C.) | 75% |
| $H_2$ Selectivity (at 850° C.) | 72% |
| CO Selectivity (at 850° C.) | 91% |
| Pressure drop | 2.1 psi |

EXAMPLE 5

A fin having the same dimensions as the fin in Example 4 is cleaned in iso-propanol for 20 min with sonication. After drying at 100° C. for 1 hour and cooling to room temperature, the fin is cleaned in 20 wt. % $HNO_3$ solution for 20 min with sonication. The fin is rinsed with deionized water until the pH value reaches 7. After drying at 120° C. for 1 hour, the fin is heated to 1000° C. in air at a heating rate of 3.5° C./min and calcined at 1000° C. for 8 hours in air. A dense $Al_2O_3$ layer is generated after calcination. The $Al_2O_3$ layer functions as a protection scale and also improves the adhesion between the coating and the fin. $Al_2O_3$ sol (25 wt. %, Sasol 14N4-25) is coated onto the fin by dipping. The excess sol is removed by jetting air over the coated surface. The fin is dried at 120° C. for 1 hour and calcined at 450° C. for 4 hours at a heating and cooling rate of 3.5° C./min. The sol coating process is repeated 3 to 4 times until 17 mg of $Al_2O_3$ loading per fin is achieved. 7.5 wt. % $La(NO_3)_3$ solution is impregnated onto the fin by dipping. The fin is dried at 120° C. for 1 hour and calcined at 1000° C. for 4 hours in air at a heating and cooling rate of 3.5° C./min. 10 wt. % $Rh(NO_3)_3$ solution is dropped onto the fin and the excess solution is blown out by compressed air. The fin is dried at 120° C. for 1 hour and calcined at 500° C. for 1 hour in air. The $Rh(NO_3)_3$ solution coating is repeated once and the fin is calcined at 1000° C. for 4 hours. The Rh loading is 5.2 mg per fin.

The resulting fin supported catalyst is tested for partial oxidation of methane to syngas at 1 atmosphere using the pellet described in Example 2. The pellet is placed in a furnace. The catalyst is reduced with $H_2$ at 450° C. for 30 min before use. The feed gas compositions were 29.6% of $CH_4$ and 70.4% of air ($CH_4/O_2$=2/1), with 2361 ml/min of total flow rate (standard conditions). The contact time is 3.3 ms. The temperature of the furnace is adjusted to keep the pellet skin temperature at mid-length at 800° C. The temperature of the feed stream at the inlet of the furnace is at room temperature. The feed stream is preheated before entering the pellet. The length of tubing from the entrance of furnace to the pellet is ten feet. The outlet pressure of the product stream is atmospheric pressure. The pressure drop in the pellet is measured by capsuhelic differential pressure gauge. The composition of product is analyzed with two-column Gas Chromatograph. The performance of the fin is measured in terms of $CH_4$ conversion, $H_2$ selectivity and CO selectivity. The performance of the fin supported catalyst after 600 hours of steady-state operation is indicated below.

| Parameter | Value |
| --- | --- |
| Coating Type | Sol wash-coat |
| Fuel composition | 29.6% $CH_4$, 70.4% air |
| Fuel contact time | 3.3 ms |
| $CH_4$ Conversion (at 800° C.) | 71% |
| $H_2$ Selectivity (at 800° C.) | 70% |
| CO Selectivity (at 800° C.) | 87% |
| Pressure drop | 1.4 psi |

The foregoing fin supported catalyst is tested with an n-butane and $CH_4$ fuel mixture. The feed gas contains 7.2% $CH_4$, 7.2% n-butane and 85.6% air with a total flow rate of 2091 ml/min. A four column gas chromatograph is used to analyze the outlet gas composition. The temperature of the furnace is adjusted to keep pellet skin temperature at mid-length at 800° C. The performance of the fin supported catalyst after 300 hours of operation is summarized below.

| Parameter | Value |
| --- | --- |
| CoatingType | Powder slurry wash-coat |
| Fuel composition | 7.5% $CH_4$, 7.5% n-butane, 85% air |
| Fuel contact time | 3.3 ms |
| $CH_4$ Conversion (at 800° C.) | 60% |
| n-butane conversion (at 800° C.) | 76% |
| $H_2$ Selectivity (at 800° C.) | 77% |
| CO Selectivity (at 800° C.) | 82% |
| Pressure drop | 1.0 psi |

EXAMPLE 6

A sorption separation unit having the design illustrated in FIG. 1 is made. A selective sorption medium sorbent is coated on the walls of the fins. The fins are made from aluminum and have a height of 1 mm, a width of 0.5 mm, and are spaced 0.5 mm apart. The base of the fin is 0.5 mm. The fin is inserted in a process microchannel with a height of 1.05 mm and a width of 5 cm. There are 50 fins within the microchannel. The process microchannel is adjacent to a heat transfer channel. Water is used as the heat transfer fluid to cool the unit for sorption and warm the unit for desorption. During desorption, a water stream at 65° C. flows through the heat exchange channel. During sorption, a water stream at 15° C. flows through the heat exchange channel.

A mixed feed of methane and nitrogen is fed to sorption unit. Methane preferentially sorbs on the sorption medium over nitrogen. Sorption occurs at 35° C. As the sorption medium is filled to capacity, the temperature of the sorption medium is increased to 55° C. by flowing a warm fluid through the heat exchange channel. The methane desorbs into the desorbant fluid which is methane or natural gas.

After desorbing the methane, the temperature of the sorption medium is cooled to 35° C. for a second cycle of sorption. The cycle time between heating and cooling is 0.1 second.

While the invention has been explained in relation to various detailed embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. An apparatus, comprising:
   at least one process microchannel having a height, width and length, the process microchannel having a base wall extending in one direction along the width of the process microchannel and in another direction along the length of the process microchannel;
   a fin assembly comprising a plurality of parallel spaced fins, the fins extending along at least part of the length of the process microchannel, the fin assembly being made separately from the microchannel and inserted into the microchannel the fin assembly providing additional support for the microchannel; and
   a catalyst or a sorption medium supported by the fins.

2. The apparatus of claim 1 wherein the at least one process microchannel comprises a plurality of process microchannels extending parallel to each other.

3. The apparatus of claim 1 wherein the process microchannel has an upper wall spaced apart from and facing the base wall, at least some of the fins extending from the base wall to the upper wall.

4. The apparatus of claim 1 wherein the process microchannel has an upper wall spaced apart from and facing the base wall, at least some of the fins extending from the base wall part way toward the upper wall.

5. The apparatus of claim 1 wherein each fin has an exterior surface and a porous material overlies at least part of the exterior surface of the fin, the catalyst or sorption medium being supported by the porous material.

6. The apparatus of claim 5 wherein the porous material comprises a coating, fibers, foam or felt.

7. The apparatus of claim 1 wherein each fin has an exterior surface and a plurality fibers or protrusions extend from at least part of the exterior surface of the fin, the catalyst or sorption medium being supported by the protrusions.

8. The apparatus of claim 1 wherein each fin has an exterior surface and the catalyst or sorption medium is: washcoated on at least part of the exterior surface of the fin; grown on at least part of the exterior surface of the fin from solution; or deposited on at least part of the exterior surface of the fin using vapor deposition.

9. The apparatus of claim 1 wherein at least some of the fins extend continuously along at least part of the length of the microchannel.

10. The apparatus of claim 1 wherein at least some of the fins extend discontinuously along at least part of the length of the microchannel.

11. The apparatus of claim 1 wherein at least some of the fins comprises a plurality of separate fin members extending along at least part of the length of the microchannel.

12. The apparatus of claim 1 wherein at least one of the fins has a length that is different than the length of the other fins.

13. The apparatus of claim 1 wherein at least one of the fins has a height that is different than the height of the other fins.

14. The apparatus of claim 1 wherein the cross sections of the fins have the shape of a square or a rectangle.

15. The apparatus of claim 1 wherein the cross sections of the fins have the shape of a trapezoid.

16. The apparatus of claim 1 wherein the process microchannel is made of a material comprising: steel; aluminum; titanium; nickel: platinum; rhodium; copper; chromium; brass; an alloy of any of the foregoing metals; a polymer; ceramics; glass; a composite comprising a polymer and fiberglass; quartz; silicon; or a combination of two or more thereof.

17. The apparatus of claim 1 wherein the fin assembly is made of a material comprising: steel; aluminum; titanium; nickel; platinum; rhodium; copper, chromium; brass; an alloy of any of the foregoing metals; a polymer; ceramics; glass; a composite comprising polymer and fiberglass; quartz; silicon; or a combination of two or more thereof.

18. The apparatus of claim 1 wherein the fin assembly is made of an alumina forming material.

19. The apparatus of claim 1 wherein the fin assembly is made of FeCrAlY.

20. The apparatus of claim 1 wherein the apparatus further comprises at least one heat exchange channel adjacent to the microchannel.

21. The apparatus of claim 20 wherein the heat exchange channel is a microchannel.

22. The apparatus of claim 20 wherein the heat exchange channel is made of a material comprising: steel; aluminum; titanium; nickel; platinum; rhodium; copper; chromium; brass; an alloy of any of the foregoing metals; a polymer, ceramics; glass; a composite comprising polymer and fiberglass; quartz; silicon; or a combination of two or more thereof.

23. The apparatus of claim 1 wherein the catalyst comprises a catalyst useful in conducting one or more of the following chemical reactions: acetylation addition, alkylation, dealkylation, hydrodealkylation, reductive alkylation, amination, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, ammoxidation, water-gas shift, dehalogenation, dimerization, epoxidation, esterification, Fischer-Tropsch reaction, halogenation, hydrohalogenation, homologation, hydration, dehydration, hydrogenation, dehydrogenation, hydrocarboxylation, hydroformylation, hydrogenolysis, hydrometallation, hydrosilation, hydrolysis, hydrotreating, isomerization, methylation, demethylation, metathesis, methanol synthesis, nitration, oxidation, partial oxidation, polymerization, reduction, reformation, reverse water gas shift, sulfonation, telomerization, transesterification, trimerization, Sabatier reaction, carbon dioxide reforming, preferential oxidation, or preferential methanation.

24. The apparatus of claim 1 wherein the catalyst comprises a metal, metal oxide or mixed metal oxide of a metal selected from Mo, W, V, Nb, Sb, Sn, Pt, Pd, Cs, Zr, Cr, Mg, Mn, Ni, Co, Ce, or a mixture of two or more thereof.

25. The apparatus of claim 1 wherein the catalyst comprises: a noble metal, a transition metal or combination thereof; an oxide of an alkali metal, alkaline earth metal, boron, gallium, germanium, arsenic, selenium, tellurium, thallium, lead, bismuth, polonium, magnesium, titanium, vanadium, chromium, manganese, iron, nickel, cobalt, copper, zinc, zirconium, molybdenum, tin, calcium, aluminum, silicon, lanthanum series element; or a combination of any two or more of the foregoing.

26. The apparatus of claim 1 wherein the sorption medium comprises silver, gold, platinum, palladium, nickel, zeolite, silica gel, or a combination of two or more thereof.

27. The apparatus of claim 1 wherein the sorption medium is derived from Fe(II), Co(II), Cu(I), V(II), Mn(II), Mn(III), Cr(II), Ag(I), Rh(I), Rh(II), Rh(III), U(IV), V(IV), Ru(II), Ru(IV), Ti(III), Cr(IV), Bi(III), Ni(II), W(V), W(IV), Mo(II), Mo(III), Mo(IV), Mo(V), Mo(VI), or a combination of two or more thereof.

28. The apparatus of claim 1 wherein the sorption medium is derived from: dipyridyl; 2,6-[1-(2-imidazol-4-ylethylimino) ethyl pyridine]; cyclen; cyclam; a Schiff base ligand; acetyl acetonate or an oligomer or polymer thereof; a carboxylate; bipyridyl or an oligomer or polymer thereof; a porphyrin or an oligomer or polymer thereof; a corin or an oligomer or polymer thereof; a polyamide; a protein; 8-hydroxy quinoline or an oligomer or polymer thereof; ethyl cysteinate or an oligomer or polymer thereof; an N-alkyl alkanohydroxamic acid; dimethylglyoxime; sym-diethylethylenediamine; or a combination of two or more thereof.

29. The apparatus of claim 1 wherein the sorption medium is derived from an imidazole, histidine amino acid, pyridine, piperidine, 4-methyl aminopyridine, 4-dimethyl aminopyridine, a nitrate, a thiocyanate, a halide, or a combination of two or more thereof.

30. The apparatus of claim 1 wherein the sorption medium comprises: hemoglobin; hemoerythyrin; hemocyanin; myoglobin; Co(II) (acacen); Co(II) (dry cave) (N-methyl imidazole); Fe(II) (H2TpivPP)B; Fe(II)(capped porphyrin)B; Fe(ophen)$_2^{2+}$; bis(ethyl cysteinato) oxovanadium (IV); Cu(I) (bimp); bis(dimethylglyoximato)cobalt(II); bis(histidine)cobalt(II); dinitrato-bis(sym-diethylethylenediamine) cobalt(II); dichloro-bis(sym-diethylethylenediamine)cobalt (II); [m-tetra(a,a,a,a-o-pivalamidophenyl)porphyrin]cobalt (II);[N,N-bis(salicylidene)dipropylenetriamine]cobalt(II); [2,3,10,11,13,19-hexamethyl-3,10,14,18,21,25-hexaazabicyclo[10.7.7]hexacosa-1,11,13,18,20,25-hexene-k$^4$N)cobalt (II)hexafluorophosphate;[N,N'-bis(salicylicylidene) ethylenediamine]cobalt(II); [N,N'-bis(3-methoxysalicylicylidene)ethylenediamine]cobalt(II); [N,N'-bis(salicylicylidene)tetramethylethylenediamine]cobalt(II); [N,N'-bis(3-methoxysalicylicylidene)tetramethylethylenediamine]cobalt(II); [N,N'-bis(3-isoprpoxysalicylicylidene)tetramethylethylenediamine]cobalt(II); [N,N'-bis(3-ethoxysalicylicylidene)tetramethylethylenediamine]cobalt(II); [N,N'-bis(5-methoxysalicylicylidene)tetramethylethylenediamine]cobalt(II); [N,N'-bis(5-n-butoxysalicylicylidene)tetramethylethylenediamine]cobalt(II); [N,N'-bis(salicylidene)ethylenediamine]cobalt(II)); a cobalt (II) porphyrin complex: a metal-cyanide complex encapsulated within a zeolite; a cyanocobaltate; hemoglobin, hemerythrin or hemocyanin containing a diiron(III,IV), dicopper(II) or dimanganese core; N,N'-disalicylideneethylenediamine cobalt(II); cobalt di-(3-methoxysalicylal tertbutylamine); [N,N'-bis(salicylidene)n-propyldipropylenetriamine]cobalt (II); 1-methylimidazole; 2-methylimidazole; 4-dimethylaminopyridine; cyanopyridine; cobalt chelated copolymer derived from ethylene-diamine-tetraacetic acid, methyl methacrylate and butyl acrylate; bis(histidine) cobalt(II); [a-mono(o-methacrylamidophenyl)-a,a,a-tris(o-pivalamidophenyl)porphinato]cobalt; [meso-a,a,a,a-tetrakis(o-pivalamidophenyl)porphinato]-iron(II); cobalt(II) meso-tetraphenyl-porphyrin; cobalt(II) meso-tetrakis(2-chlorophenyl) prophyrin; cobalt(II) meso-tetrakis(4-chlorophenyl) porphyrin; cobalt(II) meso-tetrakis(4-methoxy phenyl) porphyrin; cobalt(II) meso-tetrakis(2,4-dimethoxy phenyl) porphyrin; ruthenium (III) bis(salicylaldehyde)ethylenediimine; ruthenium (III) bis(salicylaldehyde)diethlenetriimine ruthenium (III) bis(picolinaldehyde)-o-phenylenediimine; ruthenium (III) bis(picolinaldehyde)ethylenediimine; ruthenium (III) bis(picolinaldehyde)diethylenetriimine; bis(dimethylglyoximato)nickel(II); bis(dimethylglyoximato)cobalt(II); bis (dimethylglyoximato)copper(II) dinitrato-bis(sym-diethylenediamine)cobalt(II); dithiocyanato-bis(sym-diethylethelenediamine)cobalt(II); dichloro-bis(sym-diethylethylenediamine)cobalt(II); cobalt di-(salicylal)-3,3'-diimino-di-n-propylamine; N,N'-disalicyclidene ethylene diamine cobalt (II); N,N'-ethylene-bis(5-nitro-salicylideniminato) cobalt(II), or a combination of two or more thereof.

31. The apparatus of claim 1 wherein the sorption medium comprises $Sb_2O_5$, AgO, PtO, $CrO_2$, PbO, HgO, $Cu_2O$, MnO, $Mn_2O_3$, $Bi_2O_4$, NiO, $NiO_2$, $Cu_2O_3$, SnO, $SnO_2$, $WO_2$, $WO_3$, $W_2O_5$, perfluorinated film, Pt/g-alumina, Fe/g-alumina, Cu/g-alumina, Zn/g-alumina, Co/g-alumina, zeolite, or a combination of two or more thereof.

32. The apparatus of claim 1 wherein the sorption medium comprises a metal cyanide oligomer or polymer.

33. The apparatus of claim 32 wherein the metal cyanide oligomer or polymer is represented by the formula $[Cu(I)(CN)_x]_n$, $[Fe(ii)(CN)_y]_n$ or $[Co(II)(CN)_y]_n$, wherein x is 3, y is 5 and n is a number that is at least 2.

34. The apparatus of claim 1 wherein the sorption medium comprises silica gel, foamed copdper, sintered stainless steel fiber, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylefle sulfide, polysulfone, polybutylene, or a combination of two or more thereof.

35. The appamtus of claim 1 wherein the sorption comprises a secondary amine, phenolic phosphate, phosphite, phenolic, bisphenolic, hydroxylamine, olefinic carboxylate, amino carboxylate, tocopherol, di-tertiarybutyl-p-cresol, stannous salt, stannous oxide, sorbate, polysorbate, or a combination of two or more thereof.

36. The apparatus of claim 1 wherein the sorption medium comprises a deposit derived from methane and hydrogen.

37. The apparatus of claim 1 wherein the fin assembly has a thermal conductivity of at least about 10 W/m/K.

38. The apparatus of claim 1 wherein the fin assembly comprises from 1 to about 50 fins per centimeter of width of the process microchannel.

39. The apparatus of claim 1 wherein the fin assembly further comprises a fin support, the fins being positioned on the fin support, the fin support overlying the base wall.

* * * * *